US009040491B2

(12) United States Patent
Dreyfuss et al.

(10) Patent No.: US 9,040,491 B2
(45) Date of Patent: May 26, 2015

(54) COMPOSITIONS, METHODS AND KITS BASED ON SMALL NUCLEAR RNAS

(75) Inventors: Gideon Dreyfuss, Wynnewood, PA (US); Jeongsik Yong, Broomall, PA (US); Tracey (Golembe) Polsky, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1032 days.

(21) Appl. No.: 11/897,052

(22) Filed: Aug. 29, 2007

(65) Prior Publication Data

US 2008/0194027 A1 Aug. 14, 2008

Related U.S. Application Data

(60) Provisional application No. 60/840,981, filed on Aug. 30, 2006.

(51) Int. Cl.
*C12N 15/11* (2006.01)

(52) U.S. Cl.
CPC .............. *C12N 15/111* (2013.01); *C12N 15/11* (2013.01); *C12N 2310/3519* (2013.01); *C12N 2320/32* (2013.01)

(58) Field of Classification Search
None
See application file for complete search history.

(56) References Cited

U.S. PATENT DOCUMENTS

| | | | | |
|---|---|---|---|---|
| 5,994,124 | A * | 11/1999 | Bozzoni ..................... | 435/320.1 |
| 6,004,749 | A | 12/1999 | Giordano et al. | |
| 2002/0058287 | A1* | 5/2002 | Graaf et al. .................... | 435/7.1 |
| 2003/0032027 | A1* | 2/2003 | Li et al. ............................ | 435/6 |
| 2003/0036519 | A1* | 2/2003 | Kole et al. ....................... | 514/44 |
| 2004/0137572 | A1* | 7/2004 | Finney et al. ................ | 435/69.1 |

OTHER PUBLICATIONS

Abounader, et al. (1999) Reversion of Human Glioblastoma Malignancy by U1 Small Nuclear RNA/Ribozyme Targeting of Scatter Factor/Hepatocyte Growth Factor and C-MET Expression. Journal of the National Cancer Institute, v.91(18):1548-56.*
Liu, et al. (2004) Inhibition of HIV-1 Multiplication by Antisense U7 snRNAs and siRNAs Targeting Cyclophilin A, Nucleic Acids Research, v.32(12):3752-9.*
Neuman de Vegvar et al. Molecular and Cellular Biology 1990, vol. 10, pp. 3365-3375.*
Baccon et al., "*Identification and characterization of Gemin7, a novel component of the survival of motor neuron complex.*" 2002, J. Biol. Chem. 277: 31957-31962.
Bass, "*Double-stranded RNA binding proteins and their substrates.*" 1995, Nucleic Acids Symp Ser.(33):13-5.
Brahms et al., "*Symmetrical dimethylation of arginine residues in spliceosomal Sm protein B/B' and the Sm-like protein LSm4, and their interaction with the SMN protein.*"2001, RNA 7: 1531-1542.

Branlant et al., "*U2 RNA shares a structural domain with U1, U4, and U5 RNAs.*" 1982, Embo J. 1(10):1259-1265.
Buhler et al., "*Essential role for the tudor domain of SMN in spliceosomal U snRNP assembly: implications for spinal muscular atrophy*", 1999, Hum. Mol. Genet. 8(13):2351-2357.
Burd and Dreyfuss, "*Conserved structures and diversity of functions of RNA-binding proteins,*" 1994, Science 265(5172):615-621.
Casey et al., "*Iron-responsive elements: regulatory RNA sequences that control mRNA levels and translation.*", 1988, 240(4854):924-8.
Charroux, et al., "*Gemin3: A novel DEAD box protein that interacts with SMN, the spinal muscular atrophy gene product, and is a component of gems.*", 1999, J. Cell Biol. 147(6):1181-94.
Charroux et al., "*Gemin4. A novel component of the SMN complex that is found in both gems and nucleoli.*", 2000, J. Cell Biol. 148(6):1177-86.
Cory & Adams, "*The Bcl2 family: regulators of the cellular life-or-death switch.*"2002, Nat. Rev. Cancer 2(9):647-56.
Crawford and Pardo, "*The neurobiology of childhood spinal muscular atrophy.*"1996, Neurobiol. Dis. 3(2):97-110.
Dayton et al., "*Functional analysis of CAR, the target sequence for the Rev protein of HIV-1.*", 1989, Science 246(4937):1625-9.
Feng et al., "*HIV-1 tat trans-activation requires the loop sequence within tar.*" 1988, Nature 334(6178):165-7.
Fischer and Luhrmann, "*An essential signaling role for the m3G cap in the transport of U1 snRNP to the nucleus.*"1990, Science 249(4970):786-90.
Fischer et al., "*Nucleo-cytoplasmic transport of U snRNPs: definition of a nuclear location signal in the Sm core domain that binds a transport receptor independently of the m3G cap.*", 1993, Embo J. 12(2):573-83.
Fischer et al., *The SMN-SIP1 complex has an essential role in spliceosomal snRNP biogenesis.*, 1997, Cell 90(6):1023-9.
Friesen and Dreyfuss, "*Specific sequences of the Sm and Sm-like (Lsm) proteins mediate their interaction with the spinal muscular atrophy disease gene product (SMN).*" 2000, J. Biol. Chem. 275(34):26370-5.
Golembe et al., "*Lymphotropic Herpesvirus saimiri uses the SMN complex to assemble Sm cores on its small RNAs.*"2005, Mol. Cell. Biol. 25(2):602-611.
Gubitz et al.,"*Gemin5, a novel WD repeat protein component of the SMN complex that binds Sm proteins.*", 2002, J. Biol. Chem. 277(7):5631-6.
Gubitz et al., "The SMN complex.", 2004, Exp. Cell Res. 296(1):51-56.
Hamm et al., "*Multiple domains of U1 snRNA, including U1 specific protein binding sites, are required for splicing.*", 1990, Embo J. 9(4):1237-44.
Iannaccone et al., "*Spinal muscular atrophy.*", 2004, Curr. Neurol. Neurosci. Rep. 4(1): 74-80.
Imai et al. "*A simple and rapid method for generating a deletion by PCR.*" 1991, Nucleic Acids Res. 19(10):2785.
Jones et al., "*Direct interaction of the spinal muscular atrophy disease protein SMN with the small nucleolar RNA-associated protein fibrillarin.*" 2001, J. Biol. Chem. 276(42):38645-51.
Kleinschmidt et al., "*U2 small nuclear RNP assembly in vitro.*" 1989, Nucleic Acids Res. 17(12): 4817-4828.

(Continued)

*Primary Examiner* — Tracy Vivlemore
(74) *Attorney, Agent, or Firm* — Riverside Law LLP

(57) ABSTRACT

The present invention includes methods for modulating the expression of a gene or mRNA in a cell using small nuclear RNAs comprising specific sequence and structural features and further comprising a nucleic acid cargo.

8 Claims, 26 Drawing Sheets

(56) References Cited

OTHER PUBLICATIONS

Kole et al., "RNA modulation, repair and remodeling by splice switching oligonucleotides."2004, Acta Biochim Pol. 51(2):373-8.
Le et al., "Stability of RNA stem-loop structure and distribution of non-random structure in the human immunodeficiency virus (HIV-1).", 1988, Nucl. Acids Res. 16(11):5153-68.
Lee et al., "Four novel U RNAs are encoded by a herpesvirus." 1988, Cell 54(5): 599607.
Lee et al., "Herpesvirus saimiri U RNAs are expressed and assembled into ribonucleoprotein particles in the absence of other viral genes.", 1990, J. Virol. 64(8): 3905-3915.
Liu and Dreyfuss, "A novel nuclear structure containing the survival of motor neurons protein." 1996, Embo J. 15(14):3555-3565.
Liu et al., "The spinal muscular atrophy disease gene product, SMN, and its associated protein SIP1 are in a complex with spliceosomal snRNP proteins.", 1997, Cell 90(6)1013-1021.
Luhrmann et al., "Structure of spliceosomal snRNPs and their role in pre-mRNA splicing.", 1990, Biochim. Biophys. Acta 1087(3):265-292.
Luhrmann, "Functions of U-snRNPs." 1990, Mol. Biol. Rep. 14(2-3):183-192.
Makeyev et al., "Targeting a KH-domain protein with RNA decoys." 2002, RNA 8(9):1160-1173.
Malter, "Identification of an AUUUA-specific messenger RNA binding protein." 1989, Science 246 (4930):664-66.
Mattaj and De Robertis, "Nuclear segregation of U2 snRNA requires binding of specific snRNP proteins."1985, Cell 40(1):111-118.
Mattaj et al., "Nucleocytoplasmic transport and snRNP assembly.", 1993, Mol. Biol. Rep. 18(2): 79-83.
McConnell et al., "Assembly of the U1 snRNP involves interactions with the backbone of the terminal stem of U1 snRNA.", 2003, RNA 9(2):193-201.
Meister and Fischer, "Assisted RNP assembly: SMN and PRMT5 complexes cooperate in the formation of spliceosomal UsnRNPs."2002, Embo J. 21(21): 5853-5863.
Meister et al., "Characterization of a nuclear 20S complex containing the survival of motor neurons (SMN) protein and a specific subset of spliceosomal Sm proteins.", 2000, Hum. Mol. Genet. 9(13):1977-1986.
Meister et al., "A multiprotein complex mediates the ATP-dependent assembly of spliceosomal U snRNPs.", 2001, Nat. Cell. Biol. 3(11):945-949.
Meister et al., "SMN-mediated assembly of RNPs: a complex story.", 2002, Trends Cell Biol. 12(10): 472-478.
Mercatante & Kole, "Modification of alternative splicing pathways as a potential approach to chemotherapy.", 2000, Pharmacol Ther. 85(3):237-43.
Mercatante et al. "Cellular response to an antisense-mediated shift of Bcl-x pre-mRNA splicing and antineoplastic agents.", 2002, J Biol Chem.; 277(51):49374-82.
Mourelatos et al., "SMN interacts with a novel family of hnRNP and spliceosomal proteins.", 2001, Embo J. 20(19):5443-5452.
Mourelatos et al., "miRNPs: a novel class of ribonucleoproteins containing numerous microRNAs." 2002, Genes Dev. 16(6):720-728.
Murthy et al., "Viral-encoded small RNAs in herpes virus saimiri induced tumors.", 1986, Embo J. 5(7):1625-1632.
Nagai et al., "Structure and assembly of the spliceosomal snRNPs. Novartis Medal Lecture." 2001, Biochem. Soc. Trans. 29 (Pt 2): 15-26.
Narayanan et al., "Coupled in vitro import of U snRNPs and SMN, the spinal muscular atrophy protein.", 2004, Mol. Cell 16(2):223-234.
Pellizzoni et al., "A novel function for SMN, the spinal muscular atrophy disease gene product, in pre-mRNA splicing.", 1998, Cell 95(5):615-624.
Pellizzoni et al., "SMN mutants of spinal muscular atrophy patients are defective in binding to snRNP proteins.", 1999, Proc. Natl. Acad. Sci. USA 96(20):11167-11172.
Pellizzoni et al., "The survival of motor neurons (SMN) protein interacts with the snoRNP proteins fibrillarin and GAR1.", 2001, Curr. Biol. 11(14):1079-1088.
Pellizzoni et al., "A functional interaction between the survival motor neuron complex and RNA polymerase II." 2001, J. Cell Biol. 152(1): 75-85.
Pellizzoni et al., "Purification of native survival of motor neurons complexes and identification of Gemin6 as a novel component.", 2002, J. Biol. Chem. 277(9):7540-7545.
Pellizzoni et al., "Essential role for the SMN complex in the specificity of snRNP assembly." 2002, Science 298(5599):1775-1779.
Pu et al., "plCln inhibits snRNP biogenesis by binding core splicedsomal proteins.", 1999, Mol. Cell. Biol. 19(6):4113-4120.
Raker et al., "The snRNP core assembly pathway: identification of stable core protein heteromeric complexes and an snRNP subcore particle in vitro.", 1996, Embo J. 15(9):2256-2269.
Raker et al., "Spliceosomal U snRNP core assembly: Sm proteins assemble onto an Sm site RNA nonanucleotide in a specific and thermodynamically stable manner.", 1999, Mol. Cell. Biol. 19(10):6554-6565.
Ratner et al., "Complete nucleotide sequence of the AIDS virus, HTLV-III.", 1985, Nature 313(6000):277-84.
Sontheimer and Steitz, "Three novel functional variants of human U5 small nuclear RNA." 1992, Mol. Cell. Biol. 12(2):734-746.
Sumpter et al., "In vitro reconstitution of U1 and U2 snRNPs from isolated proteins and snRNA." 1992, Mol. Biol. Rep. 16(4):229-240.
Taylor et al., "Induction of endogenous Bcl-xS through the control of Bcl-x pre-mRNA splicing by antisense oligonucleotides." 1999, Nat Biotechnol.; 17(11):1097-100.
Will and Luhrmann, "Spliceosomal UsnRNP biogenesis, structure and function.", 2001, Curr. Opin. Cell Biol. 13(3):290-301.
Yong et al., "Sequence-specific interaction of U1 snRNA with the SMN complex.", 2002, Embo J. 21(5):1188-1196.
Yong et al., "snRNAs contain specific SMN-binding domains that are essential for snRNP assembly.", 2004, Mol. Cell. Biol. 24(7):2747-2756.
Yong et al., "Why do cells need an assembly machine for RNA-protein complexes?", 2004, Trends Cell Biol. 14(5):226-232.
Zhang, et al., "The Sm-like HFQ protein increases OxyS RNA interaction with target mRNAs.", 2002, Mol. Cell. 9(1):11-22.

\* cited by examiner

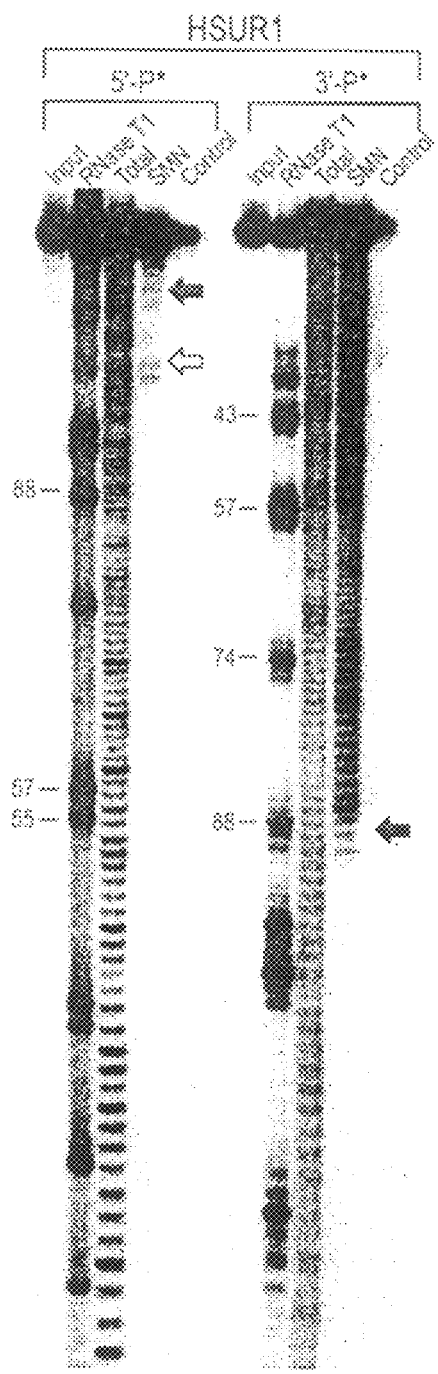
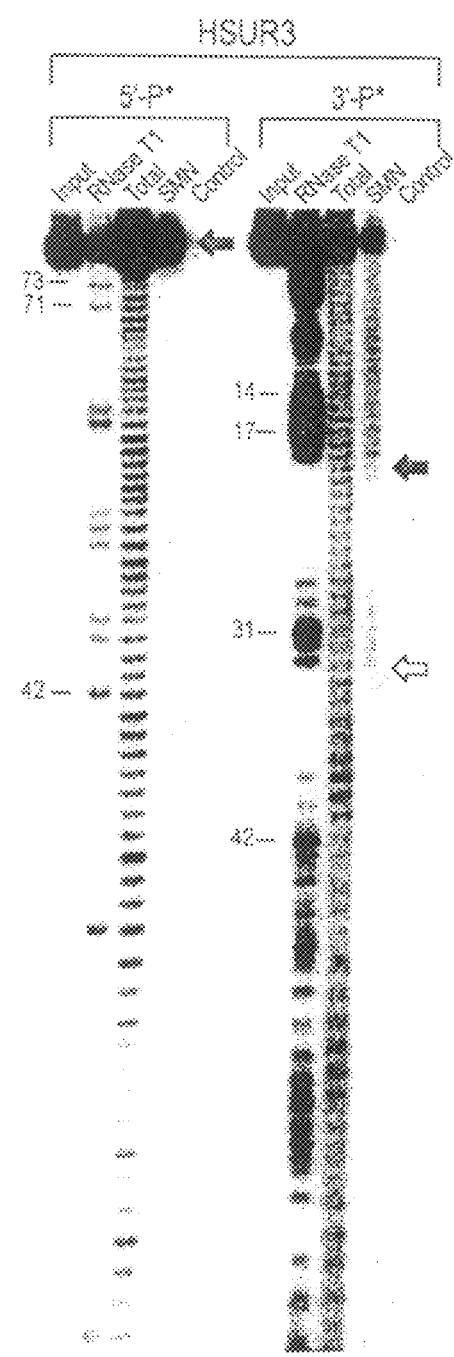
Figure 1B
Figure 1C

HSUR5-60
(SEQ ID NO. 7)

A

SEQ ID NO. 10

HSUR5-2xS
WT

B

SEQ ID NO. 11

Figure 12A
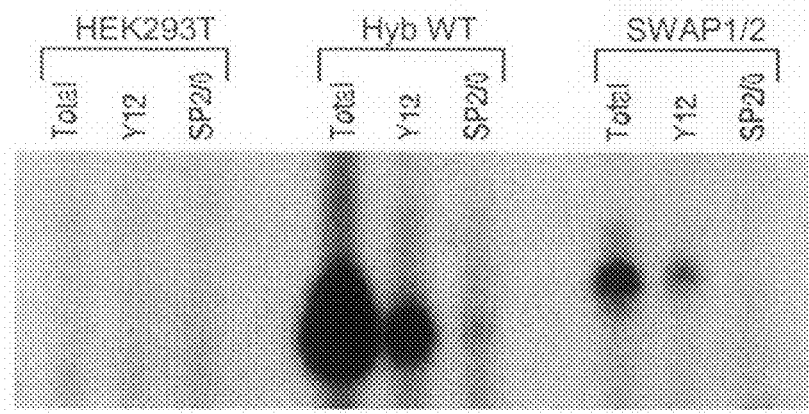
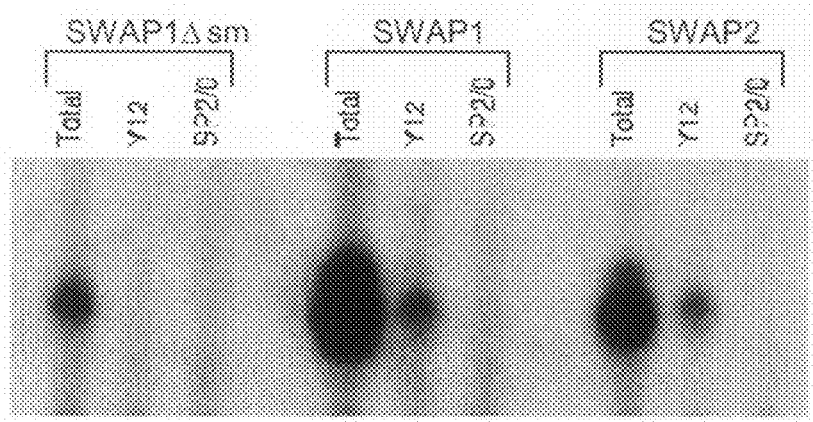
Figure 12B

SEQUENCE LISTING

<160> NUMBER OF SEQ ID NOS: 11

<210> SEQ ID NO 1
<211> LENGTH: 7
<212> TYPE: RNA
<213> ORGANISM: Artificial
<220> FEATURE:
<223> OTHER INFORMATION: Chemically synthesized

<400> SEQUENCE: 1 auuuuug                                                                          7

<210> SEQ ID NO 2
<211> LENGTH: 5
<212> TYPE: RNA
<213> ORGANISM: Artificial
<220> FEATURE:
<223> OTHER INFORMATION: Chemically synthesized

<400> SEQUENCE: 2 auuua                                                                            5

<210> SEQ ID NO 3
<211> LENGTH: 9
<212> TYPE: RNA
<213> ORGANISM: Artificial
<220> FEATURE:
<223> OTHER INFORMATION: Chemically synthesized

<400> SEQUENCE: 3 aauuucugg                                                                        9

<210> SEQ ID NO 4
<211> LENGTH: 143
<212> TYPE: RNA
<213> ORGANISM: Homo sapiens

<400> SEQUENCE: 4
gacacuacua uuuauuuauu uauuucuuag uaauguuuac uggaacuuaa aucugugaua         60
accuaaacua aaagcucuaa acaacccguu acuugcugac caauuuuugu agguacuggg        120
uguaaauaug augaccggua cca                                                143

<210> SEQ ID NO 5
<211> LENGTH: 74
<212> TYPE: RNA
<213> ORGANISM: Homo sapiens

<400> SEQUENCE: 5
gaagacugcu auaaggagau uaacacccaa gaauaauuuu ugaagcucug ggucuuuagg         60
uccaaaccag ugca                                                           74

<210> SEQ ID NO 6
<211> LENGTH: 105
<212> TYPE: RNA
<213> ORGANISM: Homo sapiens

<400> SEQUENCE: 6
ggcccacagc cagagaguua cucuucaggu ucauacaguu ggagcuucuc aguuucagaa         60
gcacucagca auuuugaag cucuggggua guccaaacca gugca                         105

<210> SEQ ID NO 7
<211> LENGTH: 114

```
<212> TYPE: RNA
<213> ORGANISM: Homo sapiens

<400> SEQUENCE: 7
gaacacuaca uauuuauuuu ucgcucgcaa agcuguaacu gaggagcaug uagucuuuuc      60
caauuaccug uucaauuuuu ggaggcaaug guguguuacu aacaaccaga gccg           114

<210> SEQ ID NO 8
<211> LENGTH: 55
<212> TYPE: RNA
<213> ORGANISM: Homo sapiens

<400> SEQUENCE: 8
ccaauuaccu guucaauuuu uggaggcaau ggugugcuuac uaacaaccag agccg          55

<210> SEQ ID NO 9
<211> LENGTH: 43
<212> TYPE: RNA
<213> ORGANISM: Homo sapiens
<220> FEATURE:
<221> NAME/KEY: misc_feature
<222> LOCATION: (1)..(6)
<223> OTHER INFORMATION: n is a, c, g, or u
<220> FEATURE:
<221> NAME/KEY: misc_feature
<222> LOCATION: (14)..(43)
<223> OTHER INFORMATION: n is a, c, g, or u

<400> SEQUENCE: 9
nnnnnnauuu uugnnnnnnn nnnnnnnnnn nnnnnnnnnn nnn                        43

<210> SEQ ID NO 10
<211> LENGTH: 87
<212> TYPE: DNA
<213> ORGANISM: Homo sapiens

<400> SEQUENCE: 10
gaatcgauaa cugaggagca uguagucuuu uuccaauuac cuguucaauu uuuggaggca      60 auggugugcuu acuaacaacc agagccg                                         87

<210> SEQ ID NO 11
<211> LENGTH: 87
<212> TYPE: DNA
<213> ORGANISM: Artificial
<220> FEATURE:
<223> OTHER INFORMATION: Chemically synthesized

<400> SEQUENCE: 11
gaatcgauaa cugaggagca uguagucuuu uuccaauuac cuguucaauu uuuggaggca      60 auggugugcuu acuaacaacc agagccg                                         87
```

COMPOSITIONS, METHODS AND KITS BASED ON SMALL NUCLEAR RNAS

CROSS REFERENCE TO RELATED APPLICATIONS

The present application claims priority under 35 U.S.C. §119(e) to U.S. Provisional Application No. 60/840,981, filed on Aug. 30, 2006, which application is incorporated by reference herein in its entirety.

STATEMENT REGARDING FEDERALLY SPONSORED RESEARCH OR DEVELOPMENT

This invention was made, in part, using funds obtained from the U.S. Government (National Institutes of Health Grant No. NS40575-03), and the U.S. Government therefore has certain rights in this invention.

BACKGROUND OF THE INVENTION

Pre-mRNA splicing takes place in the nucleus of eukaryotic cells and is mediated by the spliceosome. The major components of the spliceosome are the small nuclear ribonucleoprotein particles (snRNPs) U1, U2, U5, U4/U6, U11, U12, and U4atac/U6atac, each of which comprises one U snRNA molecule, a common core of seven Sm proteins (B/B', D1, D2, D3, E, F and G), and several snRNP-specific proteins (Luhrmann, 1990, Mol. Biol. Rep. 14: 183-192; Luhrmann, 1990, Biochim. Biophys. Acta 1087: 265-292; Will and R. Luhrmann, 2001, Curr. Opin. Cell Biol. 13: 290-301).

The biogenesis of snRNPs occurs in the cytoplasm shortly after the nuclear export of nascent snRNAs and requires the assembly of the Sm proteins into a seven-member ring (Kambach, 1999, Cell 96: 375-387; Stark, 2001, Nature 409: 539-542) on a consensus sequence (PuAU4-6GPu) known as the Sm site of the U snRNA (Branlant, 1982, EMBO J. 1: 1259-1265; Nagai, 2001, Biochem. Soc. Trans. 29: 15-26). After formation of the Sm core, the 7-methyl guanosine cap of the snRNA is hypermethylated to become a 2,2,7-trimethyl guanosine (TMG) cap (Mattaj, 1986, Cell 46: 905-911; Plessel, 1994, Mol. Cell. Biol. 14: 4160-4172). A properly assembled Sm core, cap hypermethylation and 3'-end processing are required for the translocation of the mature snRNPs into the nucleus, where they function in splicing (Fischer and Luhrmann, 1990, Science 249: 786-790; Fischer, 1993, EMBO J. 12: 573-583; Hamm, 1990, EMBO J. 9: 1237-1244; Mattaj, 1993, Mol. Biol. Rep. 18: 79-83; Mattaj and De Robertis, 1985, Cell 40: 111-118; Will and Luhrmann, 2001, Curr. Opin. Cell Biol. 13: 290-301).

The process of bringing the protein and RNA components together during U snRNP assembly in the cytoplasm is mediated by and dependent upon the survival of motor neurons (SMN) protein complex (Buhler, 1999, Hum. Mol. Genet. 8: 2351-2357; Fischer, 1997, Cell 90: 1023-1029; Liu and Dreyfuss, 1996, EMBO J. 15: 3555-3565; Liu, 1997, Cell 90: 1013-1021; Meister, 2001, Nat. Cell. Biol. 3: 945-949; Meister and Fischer, 2002, EMBO J. 21: 5853-5863; Pellizzoni, 1998, Cell 95: 615-624; Pellizzoni, 2002, Science 298: 1775-1779; Yong, 2004, Mol. Cell. Biol. 24: 2747-2756; Yong, 2002, EMBO J. 21: 1188-1196; Yong, 2004, Trends Cell Biol. 14: 226-232). Reduced levels of SMN due to a genetic defect cause spinal muscular atrophy (SMA), a severe neuromuscular disease that is characterized by degeneration of motor neurons in the spinal cord (Cifuentes-Diaz, 2002, Semin. Pediatr. Neurol. 9: 145-150; Crawford and Pardo, 1996, Neurobiol. Dis. 3: 97-110; Iannaccone, 2004, Curr. Neurol. Neurosci. Rep. 4: 74-80). SMN, as an oligomeric protein, is part of a large multi-protein complex that contains Gemin2 (Liu, 1997, Cell 90: 1013-1021), the DEAD box RNA helicase Gemin3 (Charroux, 1999, J. Cell Biol. 147: 1181-1194), Gemin4 (Charroux, 2000, J. Cell Biol. 148: 1177-1186), Gemin5 (Gubitz, 2002, J. Biol. Chem. 277: 5631-5636), Gemin6 (Pellizzoni, 2002, J. Biol. Chem. 277: 7540-7545), and Gemin7 (Baccon, 2002, J. Biol. Chem. 277: 31957-31962). Although the function of the SMN complex in snRNP assembly is its best characterized activity, it most likely functions in the assembly, metabolism and transport of various other RNPs, including snoRNPs, miRNPs, and the machineries that carry out transcription and pre-mRNA splicing (Buhler, 1999, Hum. Mol. Genet. 8: 2351-2357; Friesen and Dreyfuss, 2000, J. Biol. Chem. 275: 26370-26375; Gubitz, 2004, Exp. Cell Res. 296: 51-56; Jones, 2001, J. Biol. Chem. 276: 38645-38651; Meister, 2000, Hum. Mol. Genet. 9: 1977-1986; Mourelatos, 2001, EMBO J. 20: 5443-5452; Mourelatos, 2002, Genes Dev. 16: 720-728; Narayanan, 2004, Mol. Cell 16: 223-234; Pellizzoni, 2001, Curr. Biol. 11: 1079-1088; Pellizzoni, 1999, Proc. Natl. Acad. Sci. USA 96: 11167-11172; Pellizzoni, 2001, J. Cell Biol. 152: 75-85; Pellizzoni, 1998, Cell 95: 615-624).

Purified snRNP total proteins, a preparation referred to as TPs, readily assemble a Sm core on a minimal Sm sequence oligonucleotide in vitro without ATP hydrolysis or other non-snRNP factors (Raker, 1999, Mol. Cell. Biol. 19: 6554-6565; Raker, 1996, EMBO J. 15: 2256-2269; Sumpter, 1992, Mol. Biol. Rep. 16: 229-240). However, in cell extracts the biogenesis of U snRNPs requires ATP hydrolysis (Kleinschmidt, 1989, Nucleic Acids Res. 17: 4817-4828; Meister, 2001, Nat. Cell. Biol. 3: 945-949; Pellizzoni, 2002, Science 298: 1775-1779), indicating that snRNP proteins are not free to randomly associate with any uridine-rich RNA sequences in cells. Rather, it is the SMN complex that actively brings Sm proteins to U snRNAs, acting as a crucial specificity factor to ensure that highly stable Sm cores are only assembled on the correct snRNAs (Pellizzoni, 2002, Science 298: 1775-1779; Yong, 2004, Mol. Cell. Biol. 24: 2747-2756; Yong, 2004, Trends Cell Biol. 14: 226-232). Several components of the SMN complex bind directly to the Sm proteins, including the binding of SMN to the RG-rich C-terminal domains of the Sm proteins B, D1, and D3 (Baccon, 2002, J. Biol. Chem. 277: 31957-31962; Brahms, 2001, RNA. 7: 1531-1542; Buhler, 1999, Hum. Mol. Genet. 8: 2351-2357; Charroux, 1999, J. Cell Biol. 147: 1181-1194; Charroux, 2000, J. Cell Biol. 148: 1177-1186; Friesen and Dreyfuss, 2000, J. Biol. Chem. 275: 26370-26375; Gubitz, 2002, J. Biol. Chem. 277: 5631-5636; Liu, 1997, Cell 90: 1013-1021; Pellizzoni, 2002, J. Biol. Chem. 277: 7540-7545; Pellizzoni, 1999, Proc. Natl. Acad. Sci. USA 96: 11167-11172). This interaction is enhanced by the symmetric dimethylarginine (sDMA) modification of specific arginines by the 20S methylosome that contains an arginine methyltransferase (JBP1/PRMT5) (Friesen, 2001, Mol. Cell 7: 11111-1117; Friesen, 2001, Mol. Cell. Biol. 21: 8289-8300; Friesen, 2002, J. Biol. Chem. 277: 8243-8247; Meister, 2001, Curr. Biol. 11: 1990-1994). The SMN complex also binds directly and with sequence specificity to the Sm-site containing U snRNAs. For U1 snRNA, the SMN complex binding domain is contained within stem-loop 1 (SL1) (Yong, 2002, EMBO J. 21: 1188-1196). For the other major U snRNAs, U2, U4, and U5, the minimal SMN complex-binding domains are closer to their 3'-ends and contain the Sm site and the 3' stem-loop. These SMN complex-binding domains are necessary and sufficient for SMN complex binding and SMN-dependent assembly of Sm cores (Yong, 2004, Mol. Cell. Biol. 24: 2747-2756; Yong, 2004, Trends Cell Biol. 14: 226-232). Previous studies have suggested that the SMN complex contains at least two separate high-affinity RNA binding domains—one for U1 snRNA and the other for U2, U4 and U5 snRNAs (Yong, 2004, Mol. Cell. Biol. 24: 2747-2756; Yong, 2004, Trends Cell Biol. 14: 226-232).

The herpesvirus saimiri (HVS)-encoded small nuclear RNAs (HSURs 1-7) also use the SMN complex to assemble Sm cores (Murthy, 1986, EMBO J. 5: 1625-1632; Golembe, 2005, Mol. Cell. Biol. 25: 602-611). The HSURs bind the SMN complex with very high affinity to the U4 snRNA-type binding site and can effectively out-compete host snRNAs for snRNP assembly (Golembe, 2005, Mol. Cell. Biol. 25: 602-611). The Sm sites and predicted secondary structures of the HSURs are simple, conserved and have apparently evolved to closely resemble those of U2, U4, and U5 snRNAs (Lee, 1988, Cell 54: 599-607; Lee, 1990, J. Virol. 64: 3905-3915).

There have been many different attempts to identify small, stable and specific nucleic acids for manipulating, investigating and inhibiting the transcription and splicing complexes, and therefore gene expression. As an example, both antisense nucleotides and siRNA have been employed to silence or otherwise suppress the transcription of any number of genes. However, despite much promise and some clinical success, delivery, stability, toxicity, specificity and the delivery capacity of antisense and siRNA molecules, particularly into the cell nucleus, have always hampered this technology. The present invention addresses these issues and meets the need for small, stable, specific and deliverable gene-expression modulating nucleic acids.

BRIEF SUMMARY OF THE INVENTION

The invention includes a composition comprising an isolated snRNA, wherein the snRNA comprises (a) an Sm site, wherein the Sm site comprises an adenosine at the first position, a uridine at the second position and a uridine at the fourth position; (b) a stem-loop structure positioned 3' to the Sm site; and optionally (c) a cargo sequence comprising a nucleic acid sequence.

In this and other aspects of the invention, the cargo sequence is positioned 5' to the Sm site. Further, in this and other aspects, the cargo sequence is an antisense oligonucleotide, a small interfering RNA (siRNA), a splice-switching oligonucleotide, or an RNA binding protein decoy.

Also included in the invention is a pharmaceutical composition comprising an isolated snRNA as described.

Further included is a method of modulating the expression of a gene in a cell. The method comprises contacting the cell with an isolated snRNA as described.

There is further included in the invention a method of delivering a nucleic acid to a cell where the method comprises conjugating the nucleic acid to an isolated snRNA, wherein the snRNA is as described.

Also included is a kit for modulating the expression of a gene in a cell where the kit comprises an isolated snRNA conjugated to a cargo sequence. The kit further comprises an applicator and an instructional material for the use thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIGS. 1A through 1G, is a series of images depicting the mapping and direct binding of the minimal SMN complex-binding domains of an HSUR. FIG. 1A is an image of native SMN complexes (SMN) purified under high-salt conditions from stable cell lines expressing flag-Gemin2 and analyzed by electrophoresis on SDS-polyacrylamide gels and silver staining. Immunoprecipitation using an anti-flag antibody from the parental cell line was used as a control (Control). Core components of the SMN complex are labeled based upon molecular weight and Western blotting. FIG. 1B is an image depicting the SMN complex-binding domain of HSUR1. The 5' (5'-P*)- and 3' (3'-P*)-end-labeled HSUR1 was incubated with purified SMN complex (SMN) or nonspecific proteins purified from HeLa cells (Control). The solid arrows indicate the largest region that includes the SMN complex-binding domain, and open arrows indicate the smallest possible binding regions. FIG. 1C is an image depicting the SMN complex-binding domain of HSUR3. The same experiment as described in FIG. 1B was performed using 5'- and 3'-end-labeled HSUR3. FIG. 1D is an image depicting 5'-end deletion mutants of HSUR1 transcribed in the presence of [$^{32}$P]UTP and incubated with flag-purified SMN complex (SMN complex) or non-specific HeLa proteins (Control). FIG. 1E is an image depicting 5'-end deletion mutants of HSUR3 transcribed in the presence of [$^{32}$P]UTP and subject to SMN complex binding as described for FIG. 1D. FIG. 1F is an image of 5'-end deletion mutants of HSUR4 transcribed in the presence of [$^{32}$P]UTP and subject to SMN complex binding as described for FIG. 1D. FIG. 1G is an image of 5'-end deletion mutants of HSUR5 transcribed in the presence of [$^{32}$P]UTP and subject to SMN complex binding as described for FIG. 1D.

FIG. 2, comprising FIG. 2A through 2D depict the secondary structures of HSUR1 (SEQ ID NO. 4), HSUR3 (SEQ ID NO. 5), HSUR4 (SEQ ID NO. 6), and HSUR5 (SEQ ID NO. 7) and their SMN complex-binding domains, respectively (SMN-complex binding domains are shaded). Solid arrows designate the maximum 5'- and 3'-end boundaries of the SMN complex-binding domains, and open arrows indicate smaller domains that mediate weak binding to the SMN complex. FIG. 2E is an image depicting [$^{32}$P]UTP-labeled HSUR3, HSUR3-17, HSUR4, HSUR4-35, HSUR5, and HSUR5-60 incubated with buffer (−), HeLa mock-depleted cytoplasmic extracts (CE) or SMN complex-depleted HeLa extracts (ΔSMN) analyzed by electrophoresis on native polyacrylamide gels and autoradiography. Sm cores and free RNAs are each indicated by brackets.

FIG. 3, comprising FIG. 3A is a schematic view of a HSUR5-60 RNA used in the experiments depicted in this Figure. Arrows indicate nucleotide substitutions inserted by site-directed mutagenesis to destabilize the terminal stem of HUSR5-60 (des-stem) and +N nt indicates the addition of either 15 or 70 nucleotides added to the 3'-end of HSUR5-60 (+15 nt and +70 nt). FIG. 3B is an image depicting HSUR5-60 WT or des-stem radiolabeled at the 5'-end and incubated with the indicated dilutions of RNase T1. FIG. 3C is an image depicting radiolabeled HSUR5-60 (WT), des-stem, or +15 nt and +70 nt RNAs with mixed with U6 as a negative control and incubated with purified SMN complex. FIG. 3D is a schematic view of the experimental strategy used for Xenopus oocyte microinjection. FIG. 3E is an image depicting HSUR5-60 (WT), des-stem, or +15 nt and +70 nt RNAs labeled with [$^{32}$P]UTP, mixed with labeled U6 and injected into the cytoplasm of oocytes as depicted in FIG. 3D.

FIG. 4, comprising FIG. 4A is an image depicting HSUR5-60 (WT), des-stem, or +15 nt and +70 nt RNAs incubated with snRNP total proteins (TPs) and immunoprecipitated with anti-Sm (Y12) antibody. The composition of TPs is depicted in FIG. 4E. FIG. 4B is an image depicting the RNAs from FIG. 4A incubated with low-salt-purified SMN complex and immunoprecipitated with anti-Sm (Y12) antibody. The composition of the SMN complex is depicted in FIG. 4D. FIG. 4C is an image depicting HSUR5-60 RNA lacking the 3' stem-loop (no stem) incubated with low-salt-purified SMN complex (SMN) or TPs and then immunoprecipitated with anti-Sm (Y12) antibody. FIG. 4D is an image depicting native SMN complexes (SMN) or non-specific proteins (Control) purified from flag-Gemin2 cells or the parental HeLa cells, respectively, under low-salt conditions. FIG. 4E is an image depicting native snRNP total proteins (TPs) purified from HeLa cells and analyzed by electrophoresis on gradient polyacrylamide gels and silver staining.

FIG. 5, comprising FIG. 5A is a schematic view of the constructs used in the experiments depicted in the present Figure. FIG. 5B is an image of the wildtype (WT), Flip, Swap, and Loop constructs of HSUR4-35 and HSUR5-60, as illustrated in FIG. 5A, labeled with [$^{32}$P]UTP, mixed with U6 as a negative control and incubated with purified SMN complex. FIG. 5C is an image depicting the WT, Flip, Swap and Loop constructs of HSUR4-35 labeled with [$^{32}$P]UTP, mixed with labeled U6 and injected into the cytoplasm of Xenopus oocytes. After incubation, the oocytes were homogenized and immunoprecipitations were carried out with either anti-Sm (Y12) or control non-immune (SP2/0) antibodies. FIG. 5D is an image depicting the WT, Flip, Swap and Loop constructs of HSUR5-60 subjected to the same experimental procedures set forth for FIG. 5C.

FIG. 6, comprising FIG. 6A is an image of wild-type HSUR5-60 (AUUUUUG; SEQ ID NO:1) or HSUR5-60 in which the first or third Sm site uridine was changed to a cytosine (Sm site substitutions are indicated in bold) was [$^{32}$P]UTP-labeled, mixed with U6 as a negative control and incubated with purified SMN complex. FIG. 6A also depicts an HSUR5-60 or HSUR5-60 in which the second or fourth Sm site uridine was changed to a cytosine was subjected to SMN complex binding. FIG. 6A further depicts HSUR5-60 or HSUR5-60 in which the adenosine or guanosine was changed to a guanosine and cytosine, respectively, and was subjected to SMN complex binding. FIG. 6B is an image depicting the RNAs used in FIG. 6A incubated with low-salt-purified SMN complex and then subjected to immunoprecipitation with anti-Sm (Y12) antibody. FIG. 6C is an image depicting the RNAs used in FIG. 6A incubated with TPs and then subjected to immunoprecipitation with anti-Sm (Y12) antibody. RNAs with assembled Sm cores were isolated and analyzed by electrophoresis on polyacrylamide gels and autoradiography.

FIG. 7, comprising FIG. 7A is an image depicting the phosphorothioate interference of HSUR5-60. HSUR5-60 transcribed in the presence of A, U, G or C α-thiotriphosphate or no analog (−) was 5'-end-labeled with γ-[$^{32}$P]ATP and incubated with purified SMN complex. The Sm site is indicated by brackets. Solid circles to the right of the specified bands indicate positions where the phosphorothioate substitution interferes with SMN complex binding. FIG. 7B is an image depicting phosphorothioate interference of HSUR4-35. The same experiment as described in FIG. 7A was performed using 5'-end-labeled HSUR4-35. FIG. 7C is a graph representing kappa (κ) values for phosphorothioate interference at HSUR5-60 uridines. A κ greater than 1 signifies interference. FIG. 7D is a graph depicting kappa (κ) values for phosphorothioate interference at HSUR4-35 uridines. A κ greater than 1 signifies interference.

FIG. 8, comprising FIG. 8A is an image depicting HSUR5-60 transcribed in the presence A, U, G, or C-thiotriphosphate or no analog (−) was 5' end radio-labeled and incubated with purified TPs. Bound RNAs were immunoprecipitated with anti-Sm (Y12) antibody and cleaved with iodine, and the resulting fragments were resolved on a polyacrylamide gel. Unbound (Total) RNA was also cleaved with iodine to correct for phosphorothioate incorporation and cleavage efficiency. The Sm site is indicated by brackets. Solid circles to the right of the specified bands indicate positions where the phosphorothioate substitution interferes with TP binding and assembly. FIG. 8B is a graph depicting kappa values for phosphorothioate interference at HSUR5-60 uridines. Sm site uridines are indicated within the bracket. An increased kappa value is interpreted as interference. FIG. 8C is a schematic image depicting the secondary structure of the region of HSUR5-60 (SEQ ID NO. 8) used for phosphorothioate interference. Arrows indicate positions where phosphorothioate substitution interferes with TP binding and assembly. FIG. 8D is an image of a Western blot depicting HeLa cell extracts (Total), high-salt-purified SMN complex (SMN complex), and snRNP total proteins (TPs) run on gradient polyacrylamide gels and probed with antibodies specific for components of the SMN complex.

FIG. 10A through FIG. 10B, is a series of schematic diagram depicting HSUR5-2xSL and derivatives thereof. FIG. 10A is a schematic diagram depicting the minimal HSUR5-2xSL (SEQ ID NO. 10). The Sm site is underlined and the nucleotide cargo sequence 5' to the Sm site is shown. FIG. 10B is a schematic diagram of the plasmid constructs used to transfect HEK293T cells comprising SEQ ID NO. 11.

FIG. 1A and FIG. 1B, is a series of images depicting a gel illustrating the results of immunoprecipitation experiments. FIG. 11A is an image of a gel depicting Northern blotting hybridization with a terminal radiolabeled oligonucleotide probe complementary to HSUR5. FIG. 11B is an image of a gel depicting the results of immunoprecipitation experiments carried out on HEK293T cells transfected with the indicated plasmids. Immunoprecipitation was carried out with either control (SP2/0) or Sm (Y12) antibodies. Northern blotting hybridization with a terminal radiolabeled oligonucleptide probe complementary to HSUR5 was then performed.

FIG. 12, comprising FIG. 12A and FIG. 12B, is a series of images depicting artificial snRNAs binding to SMN. All immunoprecipitation were carried out with either an antibody directed against Sm cores (Y12) or a control antibody (SP2/0). FIG. 12A is a gel depicting immunoprecipitation experiments performed on HEK293T cells mock transfected (HEK293T), or transfected with either HybWT or SWAP1/2 plasmids. FIG. 12B is a gel depicting immunoprecipitation experiments performed on HEK293T cells transfected with either SWAP1Δsm, SWAP1, or SWAP2 plasmids.

DETAILED DESCRIPTION OF THE INVENTION

Figure 1A:
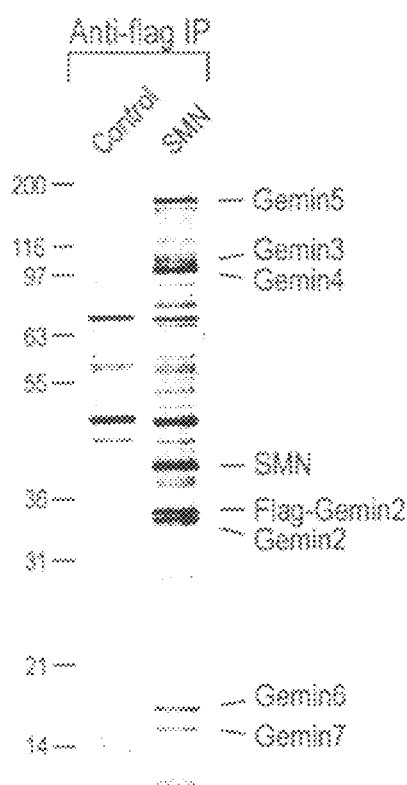

The present invention is based, in part, on the discovery of specific, conserved nucleic acid sequences and structures that are necessary for the formation of the SMN complex and Sm protein core assembly. That is, the present invention discloses specific isolated nucleic acids that are required for pre-mRNA metabolism in the nucleus. As demonstrated by the data disclosed herein, these nucleic acids target to and function in the nucleus, are stable, specific, can deliver additional nucleic acids to the nucleus, and can therefore be used to deliver antisense, interfering RNAs or decoys to RNA binding proteins, thus inhibiting gene expression in a cell, tissue or organism.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

By the term "applicator" as the term is used herein, is meant any device including, but not limited to, a hypodermic syringe, a pipette, an intravenous infusion, topical cream and the like, for administering Gemin2 inhibitor, such as a chemical compound, an antibody, a siRNA, a nucleic acid, protein, and/or composition of the invention to a mammal.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the MRNA sequence and is usually provided in sequence listings, and the non-coding strand, used as the template for transcription of a gene or cDNA, can be referred to as encoding the protein or other product of that gene or cDNA.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'-ATTGCC-5' and 3'-TATGGC-5' share 75% homology.

As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

As used herein, an "instructional material" includes a publication, a recording, a diagram, or any other medium of expression, which can be used to communicate the usefulness of the nucleic acid, peptide, and/or composition of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container, which contains the nucleic acid, peptide, chemical compound and/or composition of the invention or be shipped together with a container, which contains the nucleic acid, peptide, chemical composition, and/or composition. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids, which have been substantially purified from other components, which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized, upon the other. By way of example, a promoter operably linked to the coding region of a gene is able to promote transcription of the coding region.

Preferably, when the nucleic acid encoding the desired protein further comprises a promoter/regulatory sequence, the promoter/regulatory sequence is positioned at the 5' end of the desired protein coding sequence such that it drives expression of the desired protein in a cell. Together, the nucleic acid encoding the desired protein and its promoter/regulatory sequence comprise a "transgene."

"Constitutive" expression is a state in which a gene product is produced in a living cell under most or all physiological conditions of the cell.

"Inducible" expression is a state in which a gene product is produced in a living cell in response to the presence of a signal in the cell.

A "recombinant polypeptide" is one, which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

As used herein, to "treat" means reducing the frequency with which symptoms of the inflammatory disease, are experienced by a patient, or altering the natural history and/or progression of the disease in a patient.

As used herein, the term "antisense oligonucleotide" means a nucleic acid polymer, at least a portion of which is complementary to a nucleic acid which is present in a normal cell or in an affected cell. Most preferably, the antisense oligonucleotides comprise between about fifteen and about fifty nucleotides. The antisense oligonucleotides of the invention include, but are not limited to, phosphorothioate oligonucleotides and other modifications of oligonucleotides.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

A "portion" of a polynucleotide means at least at least about fifteen to about fifty sequential nucleotide residues of the polynucleotide. It is understood that a portion of a polynucleotide may include every nucleotide residue of the polynucleotide.

By the term "specifically binds," as used herein, is meant an antibody which recognizes and binds Gemin2, but does not substantially recognize or bind other molecules in a sample.

A "prophylactic" treatment is a treatment administered to a subject who does not exhibit signs of a disease or exhibits only early signs of the disease for the purpose of decreasing the risk of developing pathology associated with the disease.

"Preventing" a disease, as the term is used herein, means that the onset of the disease is delayed, and/or that the symptoms of the disease will be decreased in intensity and/or frequency, when a Gemin2 inhibitor is administered compared with the onset and/or symptoms in the absence of the inhibitor.

A "therapeutic" treatment is a treatment administered to a subject who exhibits signs of pathology for the purpose of diminishing or eliminating those signs.

Description

I. Compositions Comprising snRNAs

The present invention comprises an isolated small nuclear RNA (snRNA) essential to Sm core assembly, wherein the snRNA localizes to the nucleus, comprises conserved nucleotide residues and structural features, displays enhanced stability, can be expressed in cells at high levels, and is capable of delivering additional nucleic acid cargos or RNA binding protein decoys to the nucleus.

Preferably the isolated snRNA comprises several essential features that confer binding to the SMN complex and assembly of an Sm core, including: (1) an Sm site, exemplified by SEQ ID NO: 1; (2) a stem-loop structure positioned 3' to the Sm site comprising from about 7 to about 12 base pairs in the stem and from about 4 to about 17 nucleotides in the loop, where the number of nucleotides between the Sm site and the 3' stem-loop is maintained between about 1 and about 5 nucleotides; (3) a 3' end of the isolated snRNA about 5-10 nucleotides in length; (4) nucleotides located 5' to the Sm site can be about 15 nucleotides or more; and optionally (5) a nucleic acid cargo is positioned at the 5' end of the snRNA.

As demonstrated by the data disclosed herein, the present invention is not limited to the use of a Sm site set forth in SEQ ID NO: 1. That is, these data demonstrate that the first adenosine and the first and third uridine in SEQ ID NO: 1 (<u>AUU</u><u>U</u>UG; positions 1, 2 and 4) are required to interact with the SMN complex, but the additional nucleic acids set forth in SEQ ID NO: 1 are less critical and the present invention works in the manner set forth herein if such nucleic acids are mutated or otherwise altered. Thus, the present invention includes the variants of SEQ ID NO: 1 set forth herein and in the accompanying Figures.

Further, as demonstrated by the data disclosed herein, the sequence of the stem-loop is not critical to SMN binding, and thus, the present invention can comprise a modified stem-loop, providing that the stem-loop structure, as defined herein, is preserved. In addition, as demonstrated herein, the sequence of the nucleotides located at the 5' and 3' ends of the molecule are not essential to SMN binding, and thus the present invention comprises modified 5' and 3' ends of the isolated snRNA.

Therefore, the present invention should not be construed as being limited solely to the nucleic acid sequences disclosed herein. Once armed with the present invention, it is readily apparent to one skilled in the art that other isolated snRNAs can be obtained by following procedures disclosed herein, well-known in the art, or yet to be developed.

snRNA Synthesis

Any number of procedures may be used for the generation of an isolated snRNA as well as derivative or variant forms of an isolated snRNA, using recombinant DNA methodology well known in the art (see Sambrook et al., 2001, Molecular Cloning: A Laboratory Manual, Cold Spring Harbor Laboratory Press, New York; Ausubel et al., 2001, Current Protocols in Molecular Biology, Green & Wiley, New York) and by direct synthesis. For recombinant and in vitro transcription, DNA encoding RNA molecules can be obtained from known clones, by synthesizing a DNA molecule encoding an RNA molecule, or by cloning the gene encoding the RNA molecule. Techniques for in vitro transcription of RNA molecules and methods for cloning genes encoding known RNA molecules are described by, for example, Sambrook et al.

An isolated snRNA of the present invention can be produced using conventional nucleic acid synthesis or by recombinant nucleic acid methods known in the art and described elsewhere herein (2001, Molecular Cloning: A Laboratory Manual, Cold Spring Harbor Laboratory Press, New York) and Ausubel et al. (2001, Current Protocols in Molecular Biology, Green & Wiley, New York).

As an example, a method for synthesizing nucleic acids de novo involves the organic synthesis of a nucleic acid from nucleoside derivatives. This synthesis may be performed in solution or on a solid support. One type of organic synthesis is the phosphotriester method, which has been used to prepare gene fragments or short genes. In the phosphotriester method, oligonucleotides are prepared which can then be joined together to form longer nucleic acids. For a description of this method, see Narang, et al., (1979, Meth. Enzymol., 68: 90) and U.S. Pat. No. 4,356,270. The phosphotriester method can be used in the present invention to synthesize an isolated snRNA.

In addition, the compositions of the present invention can be synthesized in whole or in part, or an isolated snRNA can be conjugated to another nucleic acid using organic synthesis such as the phosphodiester method, which has been used to prepare a tRNA gene. See Brown, et al. (1979, Meth. Enzymol., 68: 109) for a description of this method. As in the phosphotriester method, the phosphodiester method involves synthesis of oligonucleotides which are subsequently joined together to form the desired nucleic acid.

A third method for synthesizing nucleic acids, described in U.S. Pat. No. 4,293,652, is a hybrid of the above-described organic synthesis and molecular cloning methods. In this process, the appropriate number of oligonucleotides to make up the desired nucleic acid sequence is organically synthesized and inserted sequentially into a vector which is amplified by growth prior to each succeeding insertion.

In addition, molecular biological methods, such as using a nucleic acid as a template for a PCR or LCR reaction, or cloning a nucleic acid into a vector and transforming a cell with the vector can be used to make large amounts of the nucleic acid of the present invention.

Nucleic Acid Cargos

In one embodiment of the invention, the isolated snRNA can accommodate large polynucleotides, referred to herein as a nucleic acid cargo, which can be positioned at the 5' end of the Sm site-stem-loop configuration without disruption of SMN binding. This nucleic acid cargo may comprise an oligonucleotide, an antisense oligonucleotide, an siRNA molecule, a splice-switching oligonucleotide, a tag, a dumbbell DNA (Lim et al., 1997, Nucleic Acid Res., 25: 575-81), or a decoy for an RNA binding protein. Further, as illustrated by the data disclosed herein, the isolated snRNA of the present invention is small, stable, and non-toxic to cells, localizes to the nucleus, and can be expressed to high levels in a cell using the vectors disclosed elsewhere herein or the methods described above. Thus, the snRNA of the present invention is a vehicle for the delivery of a nucleic acid cargo directly to the nucleus of a cell in order to modulate gene or mRNA expression. Modulate, as used herein, refers to alter, disrupt, inhibit, enhance or otherwise regulate gene and/or mRNA expression. Also encompassed within modulation of mRNA is influencing alternative splicing of mRNA.

By way of a non-limiting example, the data disclosed herein demonstrate that a nucleic acid cargo conjugated or otherwise attached to the 5' end of an isolated snRNA can comprise about 200 nucleotides without altering SMN binding, and thus, is still capable of nuclear localization and delivery of a nucleic acid cargo to the nucleus, thus inhibiting expression of the targeted gene. Thus, the present invention includes a nucleic acid cargo bound to the 5' end of an isolated snRNA comprising from about 1 to about 400 nucleotides, preferably from about 5 to about 250 nucleotides, more preferably from about 10 to about 200 nucleotides, even more preferably from about 20 to about 150 nucleotides, even more preferably from about 40 to about 100 nucleotides, preferably from about 80 to about 100 nucleotides.

Antisense Oligonucleotides

The present invention relates to snRNA that are capable of delivery cargo sequences to the nucleus. In one embodiment of the invention, these cargo sequences may comprise antisense oligonucleotides that bind to specific mRNA, pre-mRNA, or micro (mi)RNA targets. Antisense oligonucleotides directed against mRNA sequences block translation and inhibit downstream protein expression. Antisense oligonucleotides directed against miRNA modulate the miRNAs ability to repress target RNA translation or cleave mRNA. "Antisense" refers particularly to a nucleic acid sequence complementary to the target, or sense, mRNA strand, or to a sequence which is substantially homologous to the target mRNA. As defined herein, an antisense sequence is complementary to the sequence of a sense mRNA molecule. The antisense sequence may be complementary to regulatory sequences on the mRNA molecule, wherein the regulatory sequences control expression of the mRNA.

The terms "complementary" and "antisense" as used herein, are not entirely synonymous. "Antisense" refers particularly to the nucleic acid sequence that is complementary to an mRNA that is translated to a protein, or to a sequence which is substantially homologous to the translated mRNA.

The oligonucleotide agents can be synthesized in vitro by chemical synthesis. The oligonucleotide agents can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism. Modifications can also increase sequence specificity, and consequently decrease off-site targeting. Methods of synthesis and chemical modifications are described in greater detail below.

Given a sense strand sequence (e.g., the sequence of an mRNA molecule), an oligonucleotide can be designed according to the rules of Watson and Crick base pairing. The oligonucleotide can be complementary to all of or a portion of any RNA, e.g., an miRNA, pre-miRNA, or mRNA. An oligonucleotide can be, for example, from about 12 to 30 nucleotides in length, preferably about 15 to 28 nucleotides in length (e.g., 16, 17, 18, 19, 20, 21, 22, 23, 24, 25, 26, or 27 nucleotides in length, or any range derivable therein).

In other embodiments of the invention, an oligonucleotide comprises a 5' to 3' sequence that is at least 90% complementary to the 5' to 3' sequence of a target sequence. Moreover, an oligonucleotide has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a target sequence.

As used herein, "specifically hybridizable" and "complementary" are terms that are used to indicate a sufficient degree of complementarity such that stable and specific binding occurs between an oligonucleotide and a target RNA molecule, e.g., an miRNA, a pre-mRNA or an mRNA. Specific binding requires a sufficient lack of complementarity to non-target sequences under conditions in which specific binding is desired, i.e., under physiological conditions in the case of in vivo assays or therapeutic treatment, or in the case of in vitro assays, under conditions in which the assays are performed.

In one embodiment, an oligonucleotide is "sufficiently complementary" to a target mRNA, such that the oligonucleotide inhibits production of protein encoded by the target mRNA. In another embodiment, the oligonucleotide is "exactly complementary" to a target mRNA, e.g., the target mRNA and the oligonucleotide can anneal to form a hybrid made exclusively of Watson-Crick base pairs in the region of exact complementarity.

The nucleic acid cargo of the present invention is conjugated to an isolated snRNA using methods known in the art and described elsewhere herein for conjugating two or more nucleic acids. In one aspect of the invention, the nucleic acid cargo of the present invention can comprise an antisense oligonucleotide. For antisense strategies, stochiometric amounts of single-stranded nucleic acid complementary to the messenger RNA for the gene of interest are introduced into the cell. Previous difficulties with antisense-based approaches relate to delivery, stability, and dose requirements. In general, cells do not have an uptake mechanism for single-stranded nucleic acids, hence uptake of unmodified single-stranded material is extremely inefficient. While waiting for uptake into cells, the single-stranded material is subject to degradation. However, as demonstrated by the data disclosed herein, an inhibitory nucleic acid, such as an antisense oligonucleotide, conjugated to an isolated nucleic acid, is capable of delivery to the nucleus of a cell without the inherent: difficulties associated with traditional antisense delivery and use techniques.

Antisense molecules of the invention may be made synthetically and then provided to the cell using the methods of the present invention. Antisense oligomers of between about 10 to about 30, and more preferably about 15 nucleotides, are preferred, since they are easily synthesized and introduced into a target cell using an isolated snRNA. Synthetic antisense molecules contemplated by the invention include oligonucleotide derivatives known in the art which have improved biological activity compared to unmodified oligonucleotides (see Cohen, 1989, In: Oligodeoxyribonucleotides, Antisense Inhibitors of Gene Expression, CRC Press, Boca Raton, Fla.; Tullis, 1991, U.S. Pat. No. 5,023,243) incorporated by reference herein in its entirety.

The present invention contemplates using an snRNA for delivery of a nucleic acid cargo comprising class of antisense oligonucleotides known as splice-switching oligonucleotide (SSOs). SSOs are structurally similar to other antisense oligonucleotides, but are directed to mRNA sequences whereby they induce RNA repair, RNA modulation, and RNA remodeling (Kole et al., 2004, ACTA Biochemica Polonica 51:373-378). SSOs may be conjugated to snRNAs and delivered to a cell's nucleus to shift RNA splicing to favor mRNA expression that is beneficial to an individual. By way of a non-limiting example, Bcl-x, like other members of the bcl-2 family of genes is involved in apoptosis. Its two primary splice forms, bcl-xL and bcl-xS, are generated by alternative splicing of bcl-x intron 2 (Cory & Adams, 2002, Nat. Rev. Cancer 2:647-56), via the use of a common 3' splice site and two alternative 5' splice sites. Bcl-xL, the longer splice variant, is anti-apoptotic. Moreover, high levels of bcl-xL have been correlated with resistance to chemotherapy (Liu et al., 1999, Am J Pathol.; 155: 1861-7). The shorter variant, bcl-xS, which uses a 5' splice site farther upstream from the 3' splice site than bcl-xL, has been shown to have anti-apoptotic properties (Minn et al., 1996, J Biol Chem.; 271:6306-12). snRNAs conjugated to SSOs targeted against the bcl-xL 5' splice site can be used shift splicing towards production of bcl-xS (Taylor et al., 1999, Nat Biotechnol.; 17: 1097-100) to either induce apoptosis directly or enhanced the apoptotic effects of chemotherapeutics administered with the oligonucleotide. In addition, the SSO treatment may sensitized cancer cells to chemotherapeutics and radiation, or reduce resistance to anti-cancer drugs (Mercatante et al., 2002, J Biol Chem.; 277: 49374-82). SSOs can also be used to repair frame shifts (e.g. Duchenne muscular dystrophy) or to target aberrant splice sites to induce a shift from aberrant to correct splicing, thereby restoring normal protein expression. Expression of possibly thousands of alternatively spliced genes can be manipulated by SSOs either as research tools in investigations of gene function, or possibly as drugs when targeted to disease associated genes, following the example of bcl-x (Mercatante & Kole, 2000, Pharmacol Ther. 85: 237-43).

Modifications of Oligonucleotides

Oligonucleotide agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. (1994, Nucleic Acids Res. 22: 2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body.

As nucleic acids are polymers of subunits or monomers, many of the modifications described below occur at a position which is repeated within a nucleic acid, e.g., a modification of a base, or a phosphate moiety, or a non-linking O of a phosphate moiety. In some cases the modification will occur at all of the subject positions in the nucleic acid but in many, and in fact in most cases it will not. By way of example, a modification may only occur at a 3' or 5' terminal position, in a terminal region, e.g., at a position on a terminal nucleotide, or in the last 2, 3, 4, 5, or 10 nucleotides of a strand. A component can be attached at the 3' end, the 5' end, or at an internal position, or at a combination of these positions. For example, the component can be at the 3' end and the 5' end; at the 3' end and at one or more internal positions; at the 5' end and at one or more internal positions; or at the 3' end, the 5' end, and at one or more internal positions. For example, a phosphorothioate modification at a non-linking O position may only occur at one or both termini, or may only occur in a terminal region, e.g., at a position on a terminal nucleotide or in the last 2, 3, 4, 5, or 10 nucleotides of the oligonucleotide. The 5' end can be phosphorylated.

For increased nuclease resistance and/or binding affinity to the target, an oligonucleotide agent, can include, for example, 2'-modified ribose units and/or phosphorothioate linkages. E.g., the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; amine, O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

Preferred substitutents include but are not limited to 2'-methoxyethyl, 2'-OCH3, 2'-O-allyl, 2'-C-allyl, and 2'-fluoro.

"Deoxy" modifications include hydrogen (i.e. deoxyribose sugars); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

One way to increase resistance is to identify cleavage sites and modify such sites to inhibit cleavage. For example, the dinucleotides 5'-UA-3', 5'-UG-3', 5'-CA-3', 5'-UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. In certain embodiments, all the pyrimidines of the miRNA inhibitor carry a 2'-modification, and the miRNA inhibitor therefore has enhanced resistance to endonucleases.

In addition, to increase nuclease resistance, the 2' modifications can be used in combination with one or more phosphate linker modifications (e.g., phosphorothioate). The so-called "chimeric" oligonucleotides are those that contain two or more different modifications.

With respect to phosphorothioate linkages that serve to increase protection against RNase activity, the miRNA inhibitor can include a phosphorothioate at at least the first, second, or third internucleotide linkage at the 5' or 3' end of the nucleotide sequence. In one embodiment, the miRNA inhibitor includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In a preferred embodiment, the miRNA inhibitor includes at least one 2'-O-methyl-modified nucleotide, and in some embodiments, all of the nucleotides of the miRNA inhibitor include a 2'-O-methyl modification.

The 5'-terminus can be blocked with an aminoalkyl group, e.g., a 5'-O-alkylamino substituent. Other 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5' end of the oligonucleotide. Even small alkyl chains, aryl groups, or heterocyclic conjugates or modified sugars (D-ribose, deoxyribose, glucose etc.) can block 3'-5'-exonucleases.

The oligonucleotide can be constructed using chemical synthesis and/or enzymatic ligation reactions using procedures known in the art. For example, an oligonucleotide can be chemically synthesized using naturally occurring nucleotides or variously modified nucleotides designed to increase the biological stability of the molecules or to increase the physical stability of the duplex formed between the oligonucleotide and target nucleic acids, e.g., phosphorothioate derivatives and acridine substituted nucleotides can be used. Other appropriate nucleic acid modifications are described herein. Alternatively, the oligonucleotide can be produced biologically using an expression vector into which a nucleic acid has been subcloned in an antisense orientation (i.e., RNA transcribed from the inserted nucleic acid will be of an antisense orientation to a target nucleic acid of interest (e.g., an mRNA, pre-mRNA, or an miRNA).

Any polynucleotide of the invention may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

siRNA

In another embodiment of the invention, the nucleic acid cargo of the present invention comprises a small interfering RNA (siRNA). An siRNA polynucleotide is an RNA nucleic acid molecule that interferes with RNA activity that is generally considered to occur via a post-transcriptional gene silencing mechanism. An siRNA polynucleoticle preferably comprises a double-stranded RNA (dsRNA) but is not intended to be so limited and may comprise a single-stranded RNA (see, e.g., Martinez et al., 2002, Cell 110:563-74). The siRNA polynucleotide included in the invention may comprise other naturally occurring, recombinant, or synthetic single-stranded or double-stranded polymers of nucleotides (ribonucleotides or deoxyribonucleotides or a combination of both) and/or nucleotide analogues as provided herein (e.g., an oligonucleotide or polynucleotide or the like, typically in 5' to 3' phosphodiester linkage).

An siRNA may be transcribed using as a template a DNA (genomic, cDNA, or synthetic) that contains a promoter for an RNA polymerase promoter. For example, the promoter can be the U6 promoter or the H1 RNA polymerase III promoter. Alternatively, the siRNA may be a synthetically derived RNA molecule. In certain embodiments, the siRNA polynucleotide may have blunt ends. In certain other embodiments, at least one strand of the siRNA polynucleotide has at least one, and preferably two nucleotides that "overhang" (i.e., that do not base pair with a complementary base in the opposing strand) at the 3' end of either strand of the siRNA polynucleotide. In a preferred embodiment of the invention, each strand of the siRNA polynucleotide duplex has a two-nucleotide overhang at the 3' end. The two-nucleotide overhang is preferably a thymidine dinucleotide (TT) but may also comprise other bases, for example, a TC dinucleotide or a TG dinucleotide, or any other dinucleotide. The overhang dinucleotide may also be complementary to the two nucleotides at the 5' end of the sequence of the polynucleotide that is targeted for interference. For a discussion of 3' ends of siRNA polynucleotides see, e.g., WO 01/75164.

siRNA polynucleotides may comprise double-stranded polynucleotides of about 18-30 nucleotide base pairs, preferably about 18, about 19, about 20, about 21, about 22, about 23, about 24, about 25, about 26, or about 27 base pairs, and in other preferred embodiments about 19, about 20, about 21, about 22 or about 23 base pairs, or about 27 base pairs. The siRNA polynucleotide useful in the present invention may also comprise a polynucleotide sequence that exhibits variability by differing (e.g., by nucleotide substitution, including transition or transversion) at one, two, three or four nucleotides from a particular sequence. These differences can occur at any of the nucleotide positions of a particular siRNA polynucleotide sequence, depending on the length of the molecule, whether situated in a sense or in an antisense strand of the double-stranded polynucleotide. The nucleotide difference may be found on one strand of a double-stranded polynucleotide, where the complementary nucleotide with which the substitute nucleotide would typically form hydrogen bond base pairing, may not necessarily be correspondingly substituted. In preferred embodiments, the siRNA polynucleotides are homogeneous with respect to a specific nucleotide sequence.

Polynucleotides that comprise the siRNA polynucleotides of the present invention may in certain embodiments be derived from a single-stranded polynucleotide that comprises a single-stranded oligonucleotide fragment (e.g., of about 18-30 nucleotides) and its reverse complement, typically separated by a spacer sequence. According to certain such embodiments, cleavage of the spacer provides the single-stranded oligonucleotide fragment and its reverse complement, such that they may anneal to form, optionally with additional processing steps that may result in addition or removal of one, two, three or more nucleotides from the 3' end and/or the 5' end of either or both strands, the double-stranded siRNA polynucleotide of the present invention. In certain embodiments the spacer is of a length that permits the fragment and its reverse complement to anneal and form a double-stranded structure (e.g., like a hairpin polynucleotide) prior to cleavage of the spacer, and optionally, subsequent processing steps that may result in addition or removal of one, two, three, four, or more nucleotides from the 3' end and/or the 5' end of either or both strands. A spacer sequence may therefore be any polynucleotide sequence as provided herein that is situated between two complementary polynucleotide sequence regions which, when annealed into a double-stranded nucleic acid, result in an siRNA polynucleotide.

A siRNA polynucleotide sequence for use as an inhibitory nucleic acid in the methods of the present invention may be designed and chosen using computer software available commercially from various vendors, e.g., OligoEngine (Seattle, Wash.); Dharmacon, Inc. (Lafayette, Colo.); Ambion Inc. (Austin, Tex.); and QIAGEN, Inc. (Valencia, Calif.)). See also Elbashir et al., 2000 Genes & Development 15:188-200; Elbashir et al., 2001 Nature 411:494-98. The siRNA polynucleotide can then be tested for the ability to interfere with the expression of the target polypeptide according to methods known in the art. The determination of the effectiveness of a siRNA polynucleotide includes not only consideration of its ability to interfere with the expression of the target polypeptide, but also whether the siRNA polynucleotide is toxic to the host cell. For example, a desirable siRNA would exhibit an RNA interference activity and would also not exhibit an unwanted biological consequence. An example of an unwanted biological consequence is apoptosis of a cell for which cell death is not a desired as a result of the introduction of the siRNA into the host cell.

Alternatively, an siRNA polynucleotide molecule conjugated to an isolated snRNA nucleic acid can be generated by in vitro or in vivo transcription of suitable DNA sequences (e.g., polynucleotide sequences encoding a target polypeptide, or a desired portion thereof), provided that the DNA is incorporated into a vector with a suitable RNA polymerase promoter (such as for example, T7, U6, H1, or SP6 although other promoters may be equally useful).

RNA Binding Protein Decoy

The present invention further comprises the use of an RNA binding protein decoy as an inhibitory nucleic acid in the present invention. RNA binding proteins (RBP) mediate the processing of pre-mRNAs, the transport of mRNA from the nucleus to the cytoplasm, mRNA stabilization, the translational efficiency of mRNA, and the sequestration of some mRNAs. Several RNA-binding motifs exist in a many RBPs. The most common RNA binding protein motifs are the RNP motif, Arg-rich motif, RGG box, KH motif and double-stranded RNA-binding motif (Burd and Dreyfuss, 1994, Science 265:615-621). These motifs recognize both sequence and structure dependent RNA elements. In the case of the double-stranded RNA-binding motif, sequence recognition is unimportant. However, in addition to the double stranded structure, a positional effect for the double-stranded RNA may play a role in recognition (Bass, 1995, Nucleic Acids Symposium 33:13-15) and some of these proteins may also require binding to Z-DNA prior to their activity on the double-stranded RNA (Herbert et al., Proc. Natl. Acad. Sci. USA 92:7550-7554 (1995)). In addition, other RNA binding proteins, such as AUBF (Malter, Science 246:664-666 (1989)) are likely to bind in a structure-independent manner.

A number of RNA secondary structures have been identified that can be mimicked using an inhibitory nucleic acid of the present invention. Some of these include the HIV TAR structures (Feng, 1988, Nature 334, 165); including the stem loops at nucleotide 5-54, and 58-104 (Ratner, 1985, Nature 313, 277); the boundary between the EGP/OMP regions of HIV (Le, 1988, Nucl. Acids Res. 16, 5153); the boundary between the TMP/env genes of HIV (Le, 1988, Nucl. Acids Res. 16, 5153), the HIV CAR structure Dayton, 1989, Science 246, 1625); and the stem loop structure at the junction between the HIV gag and pol genes (nucleotides 1629-1674), the HIV CRS element, and the human iron responsive element (IRE) (Casey, 1988, Science 240, 024). In addition, there are regions of RNA which are primarily thought of as single stranded areas which have been identified as sites for protein binding. For example, the sequence 5'-AUUUA-3' has been identified as a signal for a protein to bind which leads to degradation of RNA (Malter, 1989, Science 246: 664).

An RNA binding protein decoy nucleic acid of the present invention includes, but is not limited to the molecules described herein, including those with the sequence AUUUA, poly(rC) molecules, a native binding target and a SELEX sequence (Makeyev et al., 2002, RNA 8: 1160-1173). Additional RNA binding protein decoy nucleic acid proteins can be identified using methods well known in the art, including those described in, for example, U.S. Pat. No. 6,004,749.

The RNA binding protein decoy nucleic acid is conjugated to an isolated snRNA according to the methods for conjugating two nucleic acids known in the art and described elsewhere herein. An isolated snRNA comprising an inhibitory nucleic acid wherein the inhibitory nucleic acid is a RNA binding protein decoy nucleic acid is delivered to a cell, tissue or organism according to the methods disclosed elsewhere herein.

Tags

In one embodiment of the invention, an isolated snRNA comprises a nucleic acid cargo comprising a covalently linked tag. That is, the invention encompasses a chimeric nucleic acid wherein the snRNA sequence comprises a tag molecule covalently linked to an isolated snRNA. Such tag molecules are well known in the art and include, for instance, a ULS reagent that reacts with the N-7 position of guanine residues, an amine-modified nucleotide, a 5-(3-aminoallyl)-dUTP, an amine-reactive succinimidyl ester moiety, a biotin molecule, $^{33}$P, $^{32}$P, fluorescent labels such as fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7.

However, the invention should in no way be construed to be limited to the nucleic acids encoding the above-listed tags. Rather, any tag which may function in a manner substantially similar to these tag polypeptides should be construed to be included in the present invention.

The snRNA comprising a tag can be used to localize an isolated snRNA within a cell, a tissue, and/or a whole organism (e.g., a mammalian embryo), detect an isolated snRNA in a cell, and to study the role(s) of an isolated snRNA in a cell. Further, addition of a tag facilitates isolation and purification of the isolated snRNA.

II. Methods

The compositions and methods of the present invention may be used to target a gene derived from any pathogen for inhibition. For example, a gene that is essential for replication of a pathogen, transmission of a pathogen, or maintenance of an infection can be inhibited using the methods and compositions of the present invention. As another example, cells at risk for infection by a pathogen or already infected cells, particularly human immunodeficiency virus (HIV) infections, may be targeted for treatment by introduction of an isolated snRNA conjugated to an inhibitory nucleic acid according to the present invention. The target gene can be a pathogen or host gene responsible for entry of a pathogen into its host, drug metabolism by the pathogen or host, replication or integration of the pathogen's genome, establishment or spread of an infection in the host, or assembly of the next generation of pathogens. Methods of prophylaxis (i.e., prevention or decreased risk of infection), as well as reduction in the frequency or severity of symptoms associated with infection, are encompassed by the present invention. The compositions and methods of the present invention can be used in combination with other treatment regimens, including virostatic and virotoxic agents, antibiotic agents, antifungal agents, anti-inflammatory agents, as well as combination therapies, and the like.

The present invention can be used for inhibiting gene expression of cancer-related genes, and is therefore a treatment or development of a treatment for cancers of any type. Thus, the inhibitory nucleic acid conjugated to an isolated snRNA can include an inhibitory nucleic acid that inhibits various cancers, including solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, in situ, Krebs 2, Merkel cell, mucinous, non-small cell lung, oat cell, papillary, scirrhous, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, cranio-pharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervical dysplasia, and for treatment of other conditions in which cells have become immortalized or transformed. The invention can also be used in combination with other treatment modalities, such as chemotherapy, cryotherapy, hyperthermia, radial-ion therapy, and the like.

As disclosed herein, the present invention is not limited to any type of target gene or nucleotide sequence. This is because, as demonstrated by the data disclosed herein, the present invention comprises a small, stable, nuclear specific delivery system for an inhibitory nucleic acid. However, the following classes of possible target genes are listed for illustrative purposes as target genes for which an inhibitory nucleic acid can be conjugated to an snRNA: developmental genes (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABL1, BCL1, BCL2, BCL6, CBFA2, CBL, CSF1R, ERBA, ERBB, EBRB2, ETS1, ETS1, ETV6, FGR, FOS, FYN, HCR, HRAS, JUN, KRAS, LCK, LYN, MDM2, MLL, MYB, MYC, MYCL1, MYCN, NRAS, PIM1, PML, RET, SRC, TALI, TCL3, and YES); tumor suppressor genes (e.g., APC, BRCA1, BRCA2, MADH4, MCC, NF1, NF2, RB1, TP53, and WT1); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases).

In another embodiment, the present invention can be used to modulate gene expression, mRNA expression, and influence mRNA splicing in a cell, tissue or organism, preferably a mammal, more preferably a human. The present invention permits the delivery of a nucleic acid cargo, such as an oligonucleotide, an siRNA, an antisense oligonucleotide, a splice-switching oligonucleotide, an RNA binding protein decoy, a dumbbell DNA, and the like, to a cell, tissue or organism. While oligonucleotides, siRNA, antisense oligonucleotides, splice-switching oligonucleotides and RNA binding protein decoys are known in the art, their promise has been hampered by a lack of adequate and effective delivery systems that permit the delivery of a nucleic acid cargo to the nucleus to modulate a gene or modify mRNA splicing.

Methods of Delivering snRNA to a Cell

The present invention comprises a method for inhibiting, manipulating, or otherwise interfering with gene expression in a cell, tissue or organism. This is because, as demonstrated by the data disclosed herein, the present invention includes an isolated snRNA that, inter alia, is essential to Sm core assembly, localizes to the nucleus, comprises conserved residues, displays remarkable stability, can be expressed at high levels, does not interact with other proteins or RNAs, and is capable of delivering additional cargo comprising nucleic acids or RNA binding protein decoys to the nucleus. Thus, the methods of the present invention include a method of inhibiting gene expression, mRNA expression, influencing alternative mRNA splicing, and a method of delivering a nucleic acid to a cell, tissue or animal, preferably a mammal, more preferably a human.

Further, as demonstrated by the data disclosed herein, the sequence of the stem-loop portion of the snRNA is not critical to SMN binding, and thus, the present invention can comprise the use of the isolated snRNA with a modified stem-loop.

The present invention should not be construed as being limited solely to the nucleic acid sequences disclosed herein in the methods of the present invention. Once armed with the present invention, it is readily apparent to one skilled in the art that other isolated snRNA can be obtained by following the procedures described herein in the experimental details section for the generation and use of other isolated snRNA as disclosed herein (e.g., site-directed mutagenesis, and the like) and procedures that are well-known in the art or to be developed, provided that the resulting snRNA comprise the canonical sequence and structural features identified herein that are necessary for snRNA interaction with the SM complex.

Isolated snRNA, either alone or preferably, conjugated or otherwise chemically bound to a cargo comprising an additional oligonucleotide, antisense oligonucleotide, splice-switching oligonucleotide, siRNA molecule, dumbbell DNA (Lim et al., 1997, Nucleic Acid Res., 25: 575-81), or decoy for an RNA binding protein (collectively referred to as a "nucleic acid cargo") can be delivered to a cell in vitro or in vivo by the use of viral vectors comprising one or more isolated snRNA sequences. Generally, the nucleic acid sequence has been incorporated into the genome of the viral vector. The viral vector comprising an isolated snRNA-inhibitory nucleic acid described herein can be contacted with a cell in vitro or in vivo and infection can occur. The cell can then be used experimentally to study, for example, the effect of an isolated snRNA in vitro, or the cells can be implanted into a subject for therapeutic use. The cell can be migratory, such as a hematopoietic cell, or non-migratory. The cell can be present in a biological sample obtained from the subject (e.g., blood, bone marrow, tissue, fluids, organs, etc.) and used in the treatment of disease, or can be obtained from cell culture and used to elucidate pre-mRNA splicing and other pre-transcription events.

After contact with the viral vector comprising an isolated snRNA-inhibitory nucleic acid sequence, the sample can be returned to the subject or re-administered to a culture of subject cells according to methods known to those practiced in the art. In the case of delivery to a subject or experimental animal model (e.g., rat, mouse, monkey, chimpanzee), such a treatment procedure is sometimes referred to as ex vivo treatment or therapy. Frequently, the cell is removed from the subject or animal and returned to the subject or animal once contacted with the viral vector comprising the isolated snRNA-inhibitory nucleic acid of the present invention. Ex vivo gene therapy has been described, for example, in Kasid, et al., Proc. Natl. Acad. Sci. USA 87:473 (1990); Rosenberg, et al, New Engl. J Med. 323:570 (1990); Williams, et al., Nature 310476 (1984); Dick, et al., Cell 42:71 (1985); Keller, et al., Nature 318:149 (1985) and Anderson, et al., U.S. Pat. No. 5,399,346 (1994).

Where a cell is contacted in vitro, the cell incorporating the viral vector comprising an isolated snRNA-inhibitory nucleic acid can be implanted into a subject or experimental animal model for delivery or used in in vitro experimentation to study cellular events mediated by an snRNA or the gene the snRNA is being used, in part, to inhibit.

Various viral vectors can be used to introduce an isolated snRNA-inhibitory nucleic acid into mammalian cells. Viral vectors include retrovirus, adenovirus, parvovirus (e.g., adeno-associated viruses), coronavirus, negative-strand RNA viruses such as orthomyxovirus (e.g., influenza virus), rhabdovirus (e.g., rabies and vesicular stomatitis virus), paramyxovirus (e.g. measles and Sendai), positive-strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g. vaccinia, fowlpox and canarypox). Other viruses include Norwalk virus, togavirus, flavivirus, reoviruses, papovirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus, lentiviruses and baculoviruses.

In addition, an engineered viral vector can be used to deliver an isolated snRNA-inhibitory nucleic acid, and accompanying antisense molecule, RNA binding protein decoy or siRNA of the present invention. These vectors provide a means to introduce nucleic acids into cycling and quiescent cells, and have been modified to reduce cytotoxicity and to improve genetic stability. The preparation and use of engineered Herpes simplex virus type 1 (D. M. Krisky, et al., Gene Therapy 4(10):1120-1125. (1997)), adenoviral (A.

Amalfitanl, et al., Journal of Virology 72(2):926-933. (1998)), attenuated lentiviral (R. Zufferey, et al., Nature Biotechnology 15(9)871-875 (1997)) and adenoviral/retroviral chimeric (M. Feng, et al., Nature Biotechnology 15(9):866-870 (1997)) vectors are known to the skilled artisan). In addition to delivery through the use of vectors, an isolated snRNA-inhibitory nucleic acid can be delivered to cells without vectors, e.g. as "naked" nucleic acid delivery using methods known to those of skill in the art. See, for example, U.S. Pat. Nos. 5,350,674 and 5,585,362.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (2001, Current Protocols in Molecular Biology, John Wiley & Sons, New York).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Various forms of an isolated snRNA-inhibitory nucleic acid, as described herein, can be administered or delivered to a mammalian cell (e.g., by virus, direct injection, or liposomes, or by any other suitable methods known in the art or later developed). The methods of delivery can be modified to target certain cells, and in particular, cell surface receptor molecules or antigens present on tumor cells. As an example, the use of cationic lipids as a carrier for nucleic acid constructs provides an efficient means of delivering the isolated snRNA-inhibitory nucleic acid of the present invention.

Various formulations of cationic lipids have been used to deliver nucleic acids to cells (WO 91/17424; WO 91/16024; U.S. Pat. Nos. 4,897,355; 4,946,787; 5,049,386; and 5,208,036). Cationic lipids have also been used to introduce foreign polynucleotides into frog and rat cells in vivo (Holt et al., Neuron 4:203-214 (1990); Hazinski et al., Am. J. Respr. Cell. Mol. Biol. 4:206-209 (1991)). Therefore, cationic lipids may be used, generally, as pharmaceutical carriers to provide biologically active substances (for example, see WO 91/17424; WO 91/16024; and WO 93/03709). Thus, cationic liposomes can provide an efficient carrier for the introduction of polynucleotides into a cell.

Further, liposomes can be used as carriers to deliver a nucleic acid to a cell, tissue or organ. Liposomes comprising neutral or anionic lipids do not generally fuse with the target cell surface, but are taken up phagocytically, and the polynucleotides are subsequently subjected to the degradative enzymes of the lysosomal compartment (Straubinger et al., Methods Enzymol. 101:512-527 (1983); Mannino et al., Biotechniques 6:682-690 (1988)). However, as demonstrated by the data disclosed herein, an isolated snRNA of the present invention is a stable nucleic acid, and thus, may not be susceptible to degradative enzymes. Further, despite the fact that the aqueous space of typical liposomes may be too small to accommodate large macromolecules, the isolated snRNA-inhibitory nucleic acid of the present invention is relatively small, and therefore, liposomes are a suitable delivery vehicle for the present invention. Methods of delivering a nucleic acid to a cell, tissue or organism, including liposome-mediated delivery, are known in the art and are described in, for example, Felgner (Gene Transfer and Expression Protocols Vol. 7, Murray, E. J. Ed., Humana Press, New Jersey, (1991)).

In other related aspects, the invention includes an isolated snRNA-inhibitory nucleic acid operably linked to a nucleic acid comprising a promoter/regulatory sequence such that the nucleic acid is preferably capable of delivering an isolated snRNA comprising an inhibitory nucleic acid. Thus, the invention encompasses expression vectors and methods for the introduction of an isolated snRNA comprising an inhibitory nucleic acid into cells.

Such delivery can be accomplished by generating a plasmid, viral, or other type of vector comprising an isolated snRNA comprising an inhibitory nucleic acid operably linked to a promoter/regulatory sequence which serves to introduce the snRNA into cells in which the vector is introduced. Many promoter/regulatory sequences useful for the methods of the present invention are available in the art and include, but are not limited to, for example, the cytomegalovirus immediate early promoter enhancer sequence, the SV40 early promoter, as well as the Rous sarcoma virus promoter, and the like. Moreover, inducible and tissue specific expression of an isolated snRNA comprising an inhibitory nucleic acid may be accomplished by placing an isolated snRNA comprising an inhibitory nucleic acid, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Selection of any particular plasmid vector or other vector is not a limiting factor in this invention and a wide plethora of vectors are well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (2001, Molecular Cloning: A Laboratory Manual, Cold Spring Harbor Laboratory, New York), and in Ausubel et al. (2001, Current Protocols in Molecular Biology, John Wiley & Sons, New York) and elsewhere herein.

The present invention includes a method of inhibiting expression of gene or other nucleic acid involved in a pathogenic disease, disorder or condition using an snRNA-inhibitory nucleic acid of the present invention. Methods for inhibiting the expression of a gene are well known to those of ordinary skill in the art and are described elsewhere herein.

The skilled artisan will appreciate, when armed with the present disclosure and the data presented herein, that inhibiting the expression of a gene related to a disease, such as an autoimmune disease, cancer, a pathogenic organism, and the like, can result in the treatment of that disease. Thus, inhibiting the activity of a gene in a cell can be used as a method of treating a cell, tissue or organism afflicted with a disease.

Pharmaceutical Compositions

Compositions comprising snRNAs and nucleic acid cargos (snRNA-cargo), can be incorporated into pharmaceutical compositions suitable for administration. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. Supplementary active compounds can also be incorporated into the compositions.

For ease of exposition, the formulations, compositions, and methods in this section are discussed largely with regard to unmodified oligonucleotide agents. It should be understood, however, that these formulations, compositions, and methods can be practiced with other oligonucleotide agents, e.g., modified oligonucleotide agents, and such practice is within the invention.

A formulated composition comprising an snRNA-cargo can assume a variety of states. In some examples, the composition is at least partially crystalline, uniformly crystalline, and/or anhydrous (e.g., less than 80, 50, 30, 20, or 10% water). In another example, the snRNA-cargo is in an aqueous phase, e.g., in a solution that includes water, this form being the preferred form for administration via inhalation.

The aqueous phase or the crystalline compositions can be incorporated into a delivery vehicle, e.g., a liposome (particularly for the aqueous phase), or a particle (e.g., a microparticle as can be appropriate for a crystalline composition). Generally, the composition comprising an snRNA-cargo is formulated in a manner that is compatible with the intended method of administration.

An snRNA-cargo preparation can be formulated in combination with another agent, e.g., another therapeutic agent or an agent that stabilizes an oligonucleoltide agent, e.g., a protein that complexes with the oligonucleotide agent. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the snRNA-cargo preparation includes another snRNA-cargo, e.g., a second snRNA-cargo that can inhibit a second gene. Still other preparations can include at least three, four, five, ten, twenty, or more different snRNA-cargo. In some embodiments where more than one snRNA-cargo is used, each snRNA-cargo is directed to different target sequences.

In another embodiment, the snRNA-cargo is administered in conjunction with another therapeutic agent such as an antibiotic, an antiviral, an anti-inflammatory, a chemotherapeutic agent, or any other therapeutic compound useful in the treatment of a particular disease or disorder. The snRNA-cargo may be administered as part of an on-going treatment regimen or therapy for a particular disease such as chemotherapy or radiation therapy for various cancers.

Pharmaceutical compositions of the invention include a pharmaceutical carrier that may contain a variety of components that provide a variety of functions, including regulation of drug concentration, regulation of solubility, chemical stabilization, regulation of viscosity, absorption enhancement, regulation of pH, and the like. The pharmaceutical carrier may comprise a suitable liquid vehicle or excipient and an optional auxiliary additive or additives. The liquid vehicles and excipients are conventional and commercially available. Illustrative thereof are distilled water, physiological saline, aqueous solutions of dextrose, and the like. For water soluble formulations, the pharmaceutical composition preferably includes a buffer such as a phosphate buffer, or other organic acid salt, preferably at a pH of between about 7 and 8. For formulations containing weakly soluble antisense compounds, micro-emulsions may be employed, for example by using a nonionic surfactant such as polysorbate 80 in an amount of 0.04-0.05% (w/v), to increase solubility. Other components may include antioxidants, such as ascorbic acid, hydrophilic polymers, such as, monosaccharides, disaccharides, and other carbohydrates including cellulose or its derivatives, dextrins, chelating agents, such as EDTA, and like components well known to those in the pharmaceutical sciences, e.g., Remingtor's Pharmaceutical Science, latest edition (Mack Publishing Company, Easton, Pa.).

Nucleic acid based cargo contemplated in the invention such as antisense oligonuceletion agents include the pharmaceutically acceptable salts thereof, including those of alkaline earths, e.g., sodium or magnesium, ammonium or $NX_4^+$, wherein X is $C_1$-$C_4$ alkyl. Other pharmaceutically acceptable salts include organic carboxylic acids such as acetic, lactic, tartaric, malic, isethionic, lactobionic, and succinic acids; organic sulfonic acids such as methanesulfonic, ethanesulfonic, and benzenesulfonic; and inorganic acids such as hydrochloric, sulfuric, phosphoric, and sulfamic acids. Pharmaceutically acceptable salts of a compound having a hydroxyl group include the anion of such compound in combination with a suitable cation such as $Na^+$, $NH_4^+$, or the like.

The snRNA-cargo of the invention may be administered into a recipient in a wide variety of ways. Preferred modes of administration are parenteral, intraperitoneal, intravenous, intradermal, epidural, intraspinal, intrastemal, intra-articular, intra-synovial, intrathecal, intra-arterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump, or via catheter.

Suitable methods for nucleic acid delivery according to the present invention are believed to include virtually any method by which a nucleic acid (e.g., DNA, RNA, including viral and nonviral vectors) can be introduced into an organelle, a cell, a tissue or an organism, as described herein or as would be known to one of ordinary skill in the art. For example, the snRNA-cargo can be administered to the subject either as a naked oligonucleotide agent, in conjunction with a delivery reagent, or as a recombinant plasmid or viral vector which expresses the oligonucleotide agent.

In addition to administration with conventional carriers, the snRNA-cargo may be administered by a variety of specialized oligonucleotide delivery techniques. Sustained release systems suitable for use with the pharmaceutical compositions of the invention include semi-permeable polymer matrices in the form of films, microcapsules, or the like, comprising polylactides, copolymers of L-glutamic acid and gamma-ethyl-L-glutamate, poly(2-hydroxyethyl methacrylate), and like materials, e.g., Rosenberg et al., International application PCT/US92/05305.

The snRNA-cargo may be encapsulated in liposomes for therapeutic delivery, as described for example in Liposome Technology, Vol. II, Incorporation of Drugs, Proteins, and Genetic Material, CRC Press. The snRNA-cargo, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, ionic surfactants such as diacetylphosphate, stearylamine, or phosphatidic acid, and/or other materials of a hydrophobic nature.

The snRNA-cargo may be conjugated to poly(L-lysine) to increase cell penetration. Such conjugates are described by Lemaitre et al., Proc. Natl. Acad. Sci. USA, 84, 648-652 (1987). The procedure requires that the 3'-terminal nucleotide be a ribonucleotide. The resulting aldehyde groups are then randomly coupled to the epsilon-amino groups of lysine residues of poly(L-lysine) by Schiff base formation, and then reduced with sodium cyanoborohydride. This procedure converts the 3'-terminal ribose ring into a morpholine structure antisense oligomers.

snRNA-cargo of the invention also include conjugates of such oligonucleotides with appropriate ligand-binding molecules. The oligonucleotides may be conjugated for therapeutic administration to ligand-binding molecules which recognize cell-surface molecules, such as according to International Patent Application WO 91/04753; The ligand-binding molecule may comprise, for example, an antibody against a cell surface antigen, an antibody against a cell surface receptor, a growth factor having a corresponding cell surface receptor, an antibody to such a growth factor, or an antibody which recognizes a complex of a growth factor and its receptor. Methods for conjugating ligand-binding molecules to oligonucleotides are detailed in WO 91/04753.

Dosage

An snRNA-cargo or pharmaceutical composition of the invention can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of snRNA-cargo (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of snRNA-cargo per kg of bodyweight. The unit dose, for example, can be administered by injection (e.g., intravenous or intramuscular, intrathecally, or directly into an organ), inhalation, or a topical application.

Delivery of an snRNA-cargo directly to an organ can be at a dosage on the order of about 0.00001 mg to about 3 mg per organ, or preferably about 0.0001-0.001 mg per organ, about 0.03-3.0 mg per organ, about 0.1-3.0 mg per organ or about 0.3-3.0 mg per organ.

In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. Alternatively, it is possible to administer the composition with a frequency of less than once per day, or, for some instances, only once for the entire therapeutic regimen.

In one embodiment, a subject is administered an initial dose, and one or more maintenance doses of an snRNA-cargo. The maintenance dose or doses are generally lower than the initial dose, e.g., one-half less of the initial dose. A maintenance regimen can include treating the subject with a dose or doses ranging from 0.01 μg to 75 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

Certain factors may influence the dosage required to effectively treat a subject, including but not limited to the severity of the disease or disorder, previous treatments, the general health and/or age of the subject, and other diseases present. It will also be appreciated that the effective dosage of the snRNA-cargo used for treatment may increase or decrease over the course of a particular treatment. Changes in dosage may result and become apparent from the results of diagnostic assays. For example, the subject can be monitored after administering an snRNA-cargo composition. Based on information from the monitoring, an additional amount of the miRNA inhibitor composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on $EC_{50}$s found to be effective in in vitro and in vivo animal models.

Therapy

Therapeutic methods include evaluating the effects of a snRNA-nucleic acid cargo on cellular processes. The method includes enhancing, reducing or eliminating activity of one or more mRNAs in a cell, thereby modulating gene expression, the method comprising introducing into a cell an snRNA-nucleic acid cargo and evaluating the effects of the nucleic acid cargo on cellular processes. The method can also include comparing one or more characteristics of a cell administered the snRNA-nucleic acid cargo with a cell not having been administered the snRNA-nucleic acid cargo. Characteristics of cells that may be evaluated are not limited. They include the following characteristics or characteristics associated with: cell proliferation, mitotic index, cell cycle, apoptosis, motility, adhesion, signal transduction, protein localization, gene expression, RNA localization, cell division, DNA replication, post-translational modification, differentiation, de-differentiation, transcriptional activation, protein activation, angiogenesis, metabolism (energy production and/or consumption), protein degradation, chromatin condensation, microtubule production, DNA replication, recombination, and DNA repair functions. It is contemplated that these characteristics may be relevant globally to the cell (for example, overall protein production reduced).

The compositions and methods of the present invention can be used in combination with other treatment regimens used to treat a variety of acute and chronic diseases and disorders, including virostatic and virotoxic agents, antibiotic agents, antifungal agents, anti-inflammatory agents, as well as combination therapies, and the like. Further, the present invention contemplates using the compositions and method of the present invention in combination with anti-cancer treatments including chemotherapy, cryotherapy, hyperthermia, radiation therapy, and the like.

As an example applicable to both therapeutic and research uses of the present invention, an isolated snRNA comprising an inhibitory nucleic acid is produced wherein the inhibitory nucleic acid sequence is determined according to the partial sequence available from an expressed sequence tag (EST). Functional alterations in growth, development, metabolism, disease resistance, or other biological processes would be indicative of the normal role of the EST's gene product.

As demonstrated by the data disclosed herein, an isolated snRNA comprising an inhibitory nucleic acid is easily introduced into an intact cell/organism, therefore lending the methods of the present invention to uses in high throughput screening (HTS). For example, an inhibitory nucleic acid can be produced by an amplification reaction using primers flanking the inserts of any gene library derived from the target cell/organism. Inserts may be derived from genomic DNA or mRNA (e.g., cDNA and cRNA). Individual clones from the library can be replicated and then isolated in separate reactions, but preferably the library is maintained in individual reaction vessels (e.g., a 96-well or 384-well microtiter plate) to minimize the number of steps required to practice the invention and to allow automation of the process. Solutions containing an isolated snRNA comprising an inhibitory nucleic acid that are capable of inhibiting the different expressed genes can be placed into individual wells positioned on a microtiter plate as an ordered array, and intact cells/organisms in each well can be assayed for any changes or modifications in behavior or development due to inhibition of target gene activity. The isolated snRNA comprising an inhibitory nucleic acid can be fed directly to, or injected into, the cell or organism containing the target gene.

Alternatively, an inhibitory nucleic acid can be produced by in vivo or in vitro transcription from an expression construct used to produce the library. The construct can be replicated as individual clones of the library and transcribed to produce the inhibitory nucleic acid; the inhibitory nucleic acid is conjugated to an isolated snRNA using methods well known in the art and each clone is fed to, or injected into, the cell or organism containing the target gene. The function of the target gene can be assayed from the effects it has on the cell or organism when gene activity is inhibited. This screening could be amenable to small subjects that can be processed in large number, for example: arabidopsis, bacteria, drosophila, fungi, nematodes, viruses, zebrafish, and tissue culture cells derived from mammals.

Kits

The invention encompasses various kits relating to modulating gene expression in a cell, tissue or organism, preferably a mammal, even more preferably a human. The kit comprises an isolated snRNA nucleic acid and can also comprise an nucleic acid cargo. In additional embodiments, the kits of the present invention comprise an isolated snRNA nucleic acid of the present invention and various reagents to conjugate a nucleic acid cargo to an snRNA nucleic acid. The kits of the present invention are useful, because, as disclosed elsewhere herein, a nucleic acid cargo conjugated to a snRNA is capable of localizing to the nucleus, has increased stability, can be expressed to high levels, acts specifically to the pre-transcription machinery, and is therefore a useful vehicle for delivering a nucleic acid cargo to the nucleus of a cell. Thus, in one aspect, the invention includes a kit for modulating the expression of a gene or mRNA. The kit comprises an effective amount of an isolated snRNA and nucleic acid cargo. The kit further comprises an applicator and an instructional material for the use thereof to be used in accordance with the teachings provided herein.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

The materials and methods used in the present invention are now described.

Plasmids for In Vitro Transcription

Plasmids for in vitro transcription of HSURs 1, 3, 4 and 5 are described in Golembe et al. (2005, Mol. Cell. Biol. 25: 602-611). Construction of all deletion mutants of HSURs 1, 3, 4 and 5 cDNAs and the HSUR-60 des-stem cDNA was carried out by PCR according to Imai et al. (1991, Nucleic Acids Res. 19: 2785). The HSUR4 and HSUR5 stem, swap and flip constructs were synthesized as DNA oligonucleotides (Dharmacon, Lafayette, Colo.) and were cloned into pGem-3Z. The +15 and +70 nucleotide RNAs were created by run-off transcription after digestion with HindIII and MseI, respectively.

Labeling RNAs

In vitro transcription and [$^{32}$P]UTP labeling of RNAs was carried out as described previously (Yong, et al., 2002, EMBO J. 21:1188-1196). [$^{32}$P]UTP-labeled RNAs were purified by electrophoresis on 7 M urea-6% polyacrylamide gels and precipitated with ethanol. RNAs were resuspended in deionized distilled water. 5'- or 3'-end labeling of HSURs was carried out as described in, for example, (Zhang, et al., 2002, Mol. Cell. 9:11-22).

Limited Alkaline Hydrolysis and Minimal Binding Analysis

Limited alkaline hydrolysis was carried out as described in, for example, (Zhang, et al., 2002, Mol. Cell. 9:11-22).

Purification of Native SMN Complex

The SMN complex was purified from flag-Gemin2 HeLa Tet-ON cells as described previously (Yong, 2004, Mol. Cell. Biol. 24: 2747-2756). The parental HeLa cell line served as a negative control. For purification of the SMN complex under low-salt conditions, SMN complex or control bound to anti-flag beads (Sigma, St. Louis, Mo.) was washed extensively with RSB100 (10 mM Tris-HCl [pH 7.5], 100 mM NaCl, 2.5 MM $MgCl_2$) containing 0.02% NP40. For complex purification under more stringent conditions, three additional washes were performed for 15 minutes each at 4° C. with 10 bead volumes of RSB-500 containing 0.02% NP-40. The bound proteins were either equilibrated with 10 bead volumes of RSB-100 containing 0.01% NP-40 for binding experiments or eluted for 1 hour at 4° C. with 3× Flag peptides (Sigma) at a final concentration of 0.5 mg/ml for analysis by silver staining or Western blot. Proteins were resolved on SDS-12.5% polyacrylamide gels or NuPAGE® Novex Bis-Tris pre-cast gradient 4-12% mini-gels (Invitrogen, La Jolla, Calif.).

The following mouse monoclonal antibodies were used for Western blot: 2B1 (anti-SMN), 12H12 (anti-Gemin3), 17D10 (anti-Gemin4), 10G11 (anti-Gemin5), Y12 (anti-Sin) and 3C2 (hnRNP K). A rabbit polyclonal antibody was used to detect Gemin6.

In Vitro Binding of RNAs

In vitro binding experiments were performed as previously described (Yong, 2004, Mol. Cell. Biol. 24: 2747-2756). The bound RNAs were isolated and analyzed by electrophoresis on 7 M urea-8% polyacrylamide gels.

Preparation of HeLa Cell Cytoplasmic Extracts

HeLa cell cytoplasmic extracts competent for snRNP assembly were prepared as described previously (Yong, 2004, Mol. Cell. Biol. 24: 2747-2756) and immunodepletion of SMN complex was performed as described by Golembe et al. (2005, Mol. Cell. Biol. 25: 602-611) using anti-SMN monoclonal antibody (2B1).

Assay for Assembly of snRNPs

In vitro Sm core assembly and electrophoretic mobility shift assays were carried out as described previously (Pellizzoni, 2002, J. Biol. Chem. 277: 7540-7545). To quantitate the Sm core assembly, assembly reaction products were incubated with 4 µg anti-Sm (Y12) monoclonal antibody or control antibody (SP2/0) conjugated to Protein A Sepharose™ CL-4B (Amersham, Piscataway, N.J.) in RSB-500 (10 mM Tris-HCl [pH 7.5], 500 mM NaCl, 2.5 mM $MgCl_2$) containing 0.1% NP-40 and 2 mg/ml heparin for 1 hour at 4° C. Subsequently, the beads were washed five times with binding buffer, treated with proteinase K and the immunoprecipitated RNAs were purified by phenol-chloroform extraction and ethanol precipitation. RNAs were analyzed by electrophoresis on 7 M urea-8% polyacrylamide gels and autoradiography.

RNase T1 Digestion

HSUR5-60 RNAs were labeled at the 5' end with [γ-$^{32}$P] ATP as described in Zhang, et al. (2002, Mol. Cell 9: 11-22), and 20,000 cpm of each RNA was then incubated with RNase T1 (Ambion, The Woodlands, Tex.) according to the manufacturer's protocol. Digested RNAs were treated with proteinase K, and the RNAs were purified by phenolchloroform extraction and ethanol precipitation and analyzed by electrophoresis on 7 M urea-12% polyacrylamide gels and autoradiography.

Phosphorothioate Interference Mapping

HSUR4-35 and HSUR5-60 RNAs were transcribed using T7 polymerase in the presence of adenosine, uridine, guanosine or cytidine (A, U, G or C) α-thiotriphosphates (Glen Research, Sterling, Va.) as described by Ryder et al. (2000, Methods Enzymol. 317: 92-109). The RNAs were purified by electrophoresis on 7 M urea-6% polyacrylamide gels, precipitated with ethanol and labeled at the 5' end with γ-[$^{32}$P] ATP as described previously (Zhang, 2002, Mol. Cell 9: 11-22). 100,000 cpm of each RNA was incubated with high-salt-washed SMN complex or nonspecific purified HeLa cell proteins immobilized on anti-flag beads (Sigma) in RSB100 (10 mM Tris-HCl [pH 7.5], 100 mM NaCl, 2.5 mM $MgCl_2$) containing 0.01% NP-40 for 1 hour at 4° C. in the presence of 1 µM tRNA.

For interference with TPs, 500,000 cpm of HSUR5-60 was incubated with purified TPs for 1 hours at 30° C. in RSB100 buffer. RNAs with assembled Sm cores were purified as described for snRNP assembly. Subsequently, the beads were washed 5 times with binding buffer, treated with proteinase K, and the RNA was purified by phenolchloroform extraction and ethanol precipitation. Precipitated RNAs were resuspended in 10 µL loading buffer and cleaved at sites of phosphorothioate incorporation by addition of ⅒ volume of 2 mM $I_2$ in ethanol. Equivalent cpm counts of RNA not subjected to SMN complex binding (input) were cleaved with $I_2$ and run in parallel to normalize for phosphorothioate incorporation. The RNA fragments were resolved on either 7 M urea-10% or 12% polyacrylamide sequencing gels for HSUR4-35 and HSUR5-60, respectively, and band intensities were quantified by PhosphorImager analysis. The interference value, Kappa (κ), at each position was calculated as described by McConnell et al. (2003, RNA 9: 193-201) and is the ratio of phosphorothioate incorporated over the phosphorothioate bound in the particle. According to Ryder et al. (2000, Methods Enzymol. 317: 92-109), κ values >2 indicate interference and values <0.5 indicate enhancements.

Purification of Native snRNP Total Proteins

Native snRNP total proteins (TPs) were prepared as described previously (Sumpter et al., 1992, Mol. Biol. Rep. 16: 229-240). HeLa U snRNPs were immunopurified using anti-2,2,7Trimethylguanosine (Mouse) Agarose Conjugate (Calbiochem, La Jolla, Calif.). Proteins were resolved on NuPAGE® Novex Bis-Tris pre-cast 4-12% mini-gels (Invitrogen) and analyzed by silver staining or Western blot.

Xenopus Oocyte Microinjections

Injections were carried out as described in Fischer et al (1997, Cell 90: 1023-1029). Briefly, oocytes were harvested and incubated for 2 hours in modified Barth's solution containing 0.2% collagenase type II (Sigma). Defolliculated stage V and VI oocytes were collected and used the next day for microinjection. In a typical injection experiment, 20 nl of $^{32}$P-labeled RNAs (usually ~1×10$^6$ c.p.m.µl for each RNA) were injected into the cytoplasm of oocytes. After 1.5 hours of incubation, total extract was made and subjected to immunoprecipitation as described above for snRNP assembly.

Example 1

Identification of Sequence and Structural Elements of RNA Binding to the SMN Complex The survival of motor neurons (SMN) complex is essential for the biogenesis of spliceosomal small nuclear ribonucleoproteins (snRNPs) as it binds to and delivers Sm proteins for assembly of Sm cores on the abundant small RNAs (snRNAs). The conserved snRNAs encoded by the lymphotropic Herpesvirus saimiri (HVS) were used to determine the specific sequence and structural features of RNAs for binding to the SMN complex and for Sm core assembly. As demonstrated by the data disclosed herein, the minimal SMN complex-binding domain in a snRNA, except U1, comprises a Sm site (AUUUUUG; SEQ ID NO: 1) and an adjacent 3' stem-loop. The SMN complex requires the adenosine and the first and third uridines of the Sm site, and it directly contacts the backbone phosphates of these uridines. The specific sequence of the adjacent stem (7-12 base pairs)-loop (4-17 nucleotides) is not critical for SMN complex binding. This structural configuration is necessary and sufficient for SMN-complex binding, but for Sm core assembly, the complex also requires that the stem-loop be located within a short distance of the 3' end of the RNA, both in vitro and in vivo. As disclosed herein, these requirements are discerned by the SMN complex and not by the Sm proteins, which can bind to and assemble on a Sm site sequence alone. These results identify the defining characteristics of Sm core-containing snRNAs, and demonstrate that the SMN complex is the decoder of snRNAs.

The SMN Complex Binds to Specific and Conserved Domains of the HSURs

Previous mapping of the SMN complex-binding domains of U2, U4, and U5 snRNAs demonstrated that the SMN complex binds to regions close to the 3'-ends of these RNAs, including the Sm site and the 3' stem-loop (Yong, 2004, Mol. Cell. Biol. 24: 2747-2756). To investigate if this minimal binding domain is conserved among other Sm site-containing RNAs, limited alkaline hydrolysis was performed on HSURs and their binding to the SMN complex was measured. HSUR1 or HSUR3, labeled at the 5'- or 3'-end, were subjected to partial alkaline hydrolysis, and the resulting hydrolyzed RNA ladders were incubated with high-salt-purified SMN complexes (FIG. 1A). As illustrated in FIG. 1A, under these conditions, there is no detectable association of SMN complex with Sm proteins. The SMN-specific band below the 31 kDa marker is an antibody light chain. Bound RNAs were purified and analyzed by denaturing polyacrylamide gel electrophoresis. This method allows a rough delineation of the regions of the RNAs that may be necessary or dispensable for binding to the SMN complex.

Figure 1D:
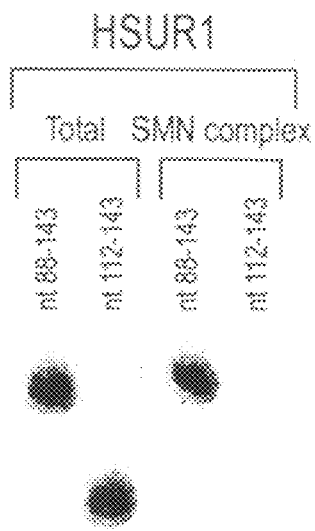
Figure 1E:
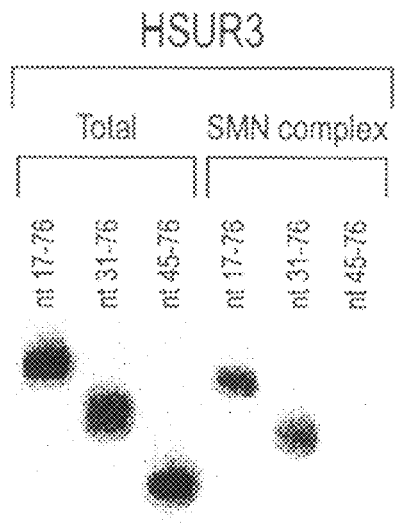

FIG. 1B depicts the SMN complex-binding domain of HSUR1. Briefly, the 5' (5'-P*)- and 3'(3'-P*)-end-labeled HSUR1 was subjected to limited alkaline hydrolysis and the resulting hydrolyzed RNA ladders were incubated with purified SMN complex (SMN) or nonspecific proteins purified from HeLa cells (Control). The RNA fragments bound to the SMN complex were isolated and analyzed by electrophoresis on urea-acrylamide gels. The full-length RNA was digested with RNase T1 to provide a size marker. The solid arrows indicate the largest region that includes the SMN complex-binding domain, and open arrows indicate the smallest possible binding regions. FIG. 1B illustrates that the domain of HSUR1 that is required for SMN complex binding contains, at most, the region between nucleotide 88 and the 3' end (nucleotide 143). Efficient binding of the SMN complex to HSUR3 requires nucleotides 17 thru the 3' end, although an even smaller region, beginning with nucleotide 31, may be sufficient for weaker binding (FIG. 1C). To confirm that the regions delineated by these mapping experiments are sufficient for SMN complex binding, the RNA fragments mapped in FIG. 1B and FIG. 1C were produced by transcription in vitro in the presence of [$^{32}$P]UTP and tested for direct binding to purified SMN complex. FIG. 1D and FIG. 1E demonstrate that the minimal regions of HSUR1 and HSUR3, respectively, are sufficient for binding to the SMN complex. Thus, similar to U2, U4 and U5 snRNAs, the regions of HSUR1 and HSUR3 necessary for SMN complex binding include both the Sm site and the 3' terminal stem-loop.

Figure 1F:
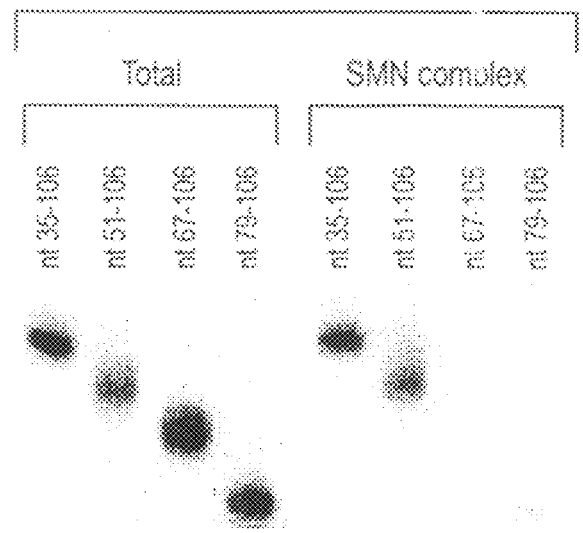
Figure 1G:
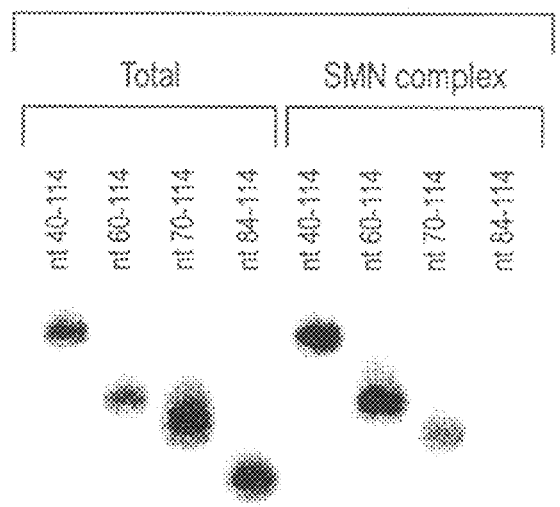
Figure 2A:
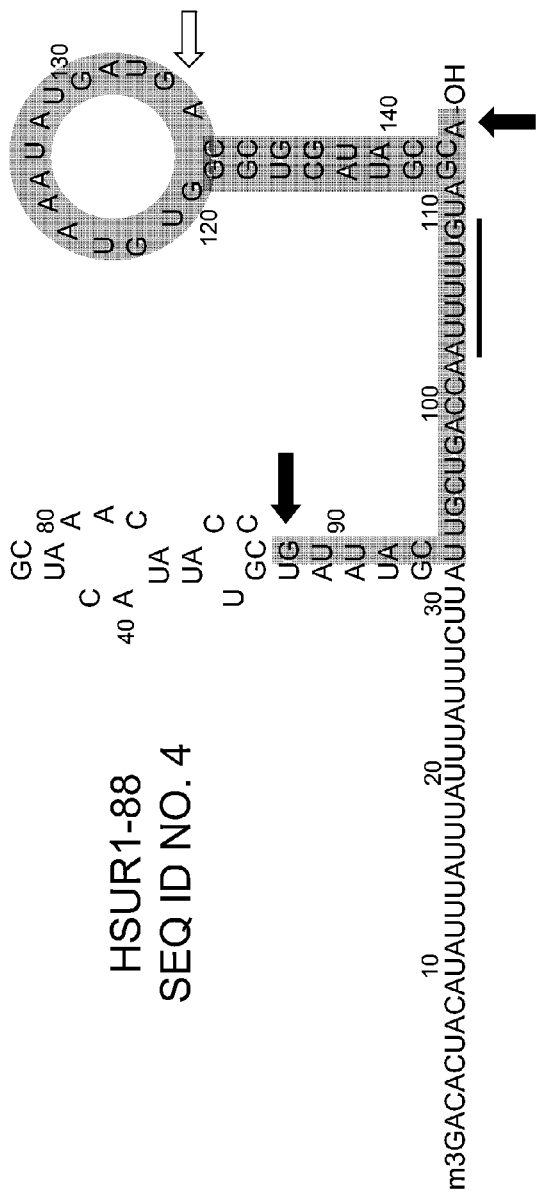
FIGS. 2A through 2E, is a series of images depicting the fact that the minimal SMN complex-binding domains are sufficient for SMN dependent Sm core assembly.

To define the SMN complex-binding domains of HSUR4 and HSUR5, the alkaline hydrolysis data described above was used as a guide, and a series of 5'-end deletion mutants were produced. RNA fragments were transcribed in the presence of [$^{32}$P]UTP, incubated with purified SMN complex or with nonspecific proteins as a control, and bound RNAs were purified. Among the deletion mutants of HSUR4, the region from nucleotide 35 thru the 3'-end (nucleotide 106) binds efficiently to the SMN complex, while the smaller fragment, beginning with nucleotide 51, binds more weakly (FIG. 1F). In the case of HSUR5, the region from nucleotide 60 thru the 3'-end (nucleotide 114) efficiently binds to the SMN complex, but the fragment that begins with nucleotide 70 is an even shorter domain that mediates weak binding (FIG. 1G). Similar to HSURs 1 and 3, the minimal regions of HSURs 4 and 5 that are necessary for SMN complex binding also contain the Sm sites and the 3' terminal stem-loops. For HSURs 1-4, the 3' stem-loop alone was tested for binding, but was not sufficient (FIGS. 1D through 1G). Overall, the minimal SMN complex-binding domains of HSURs 1-4, as indicated in FIG. 2A, resemble those for U2, U4 and U5 snRNAs and highlight the overall conservation of SMN complex-binding domains among Sm site-containing snRNAs.

Figures 2B, 2C:
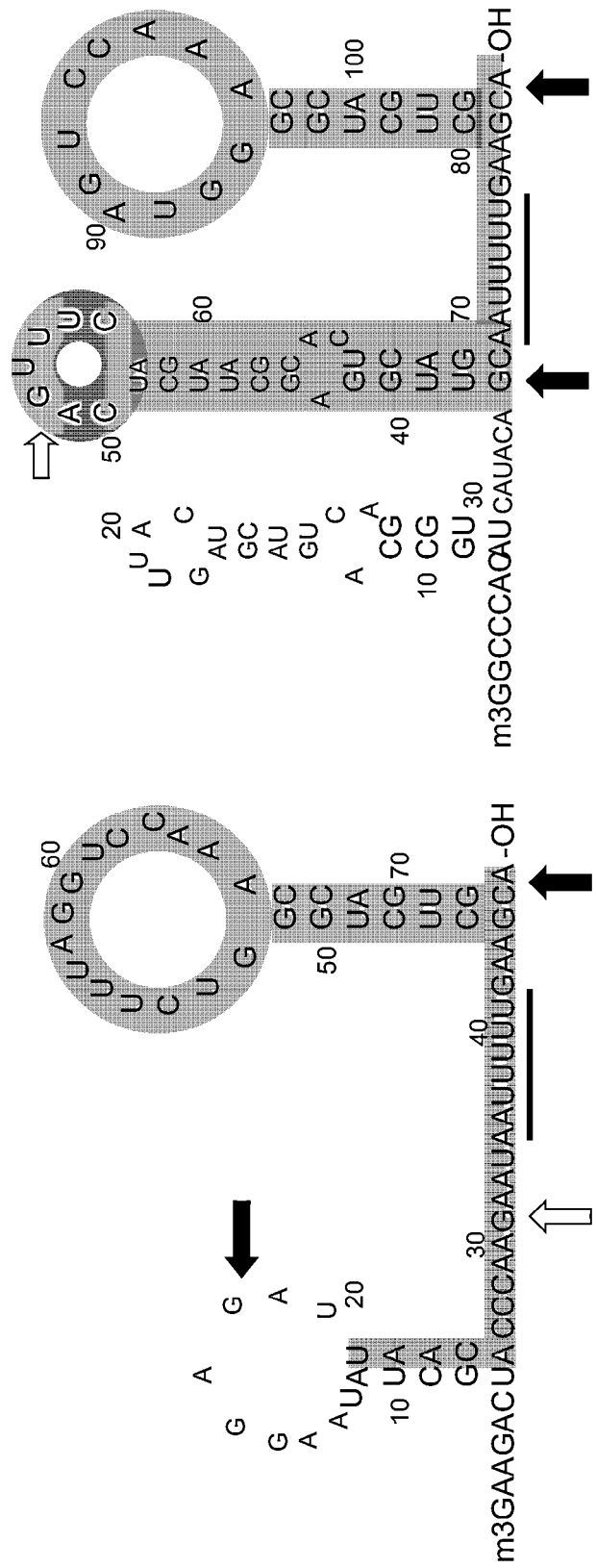
Figure 2D:
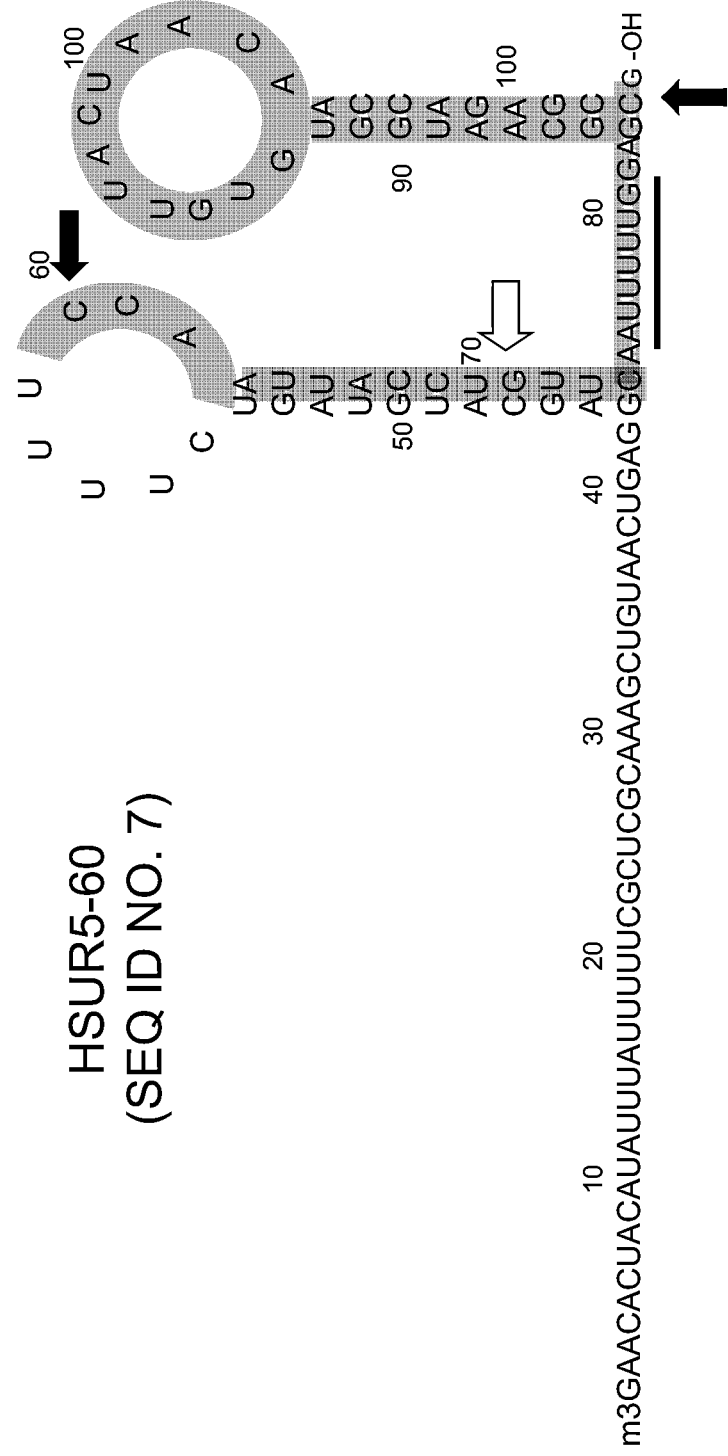
Figure 2E:
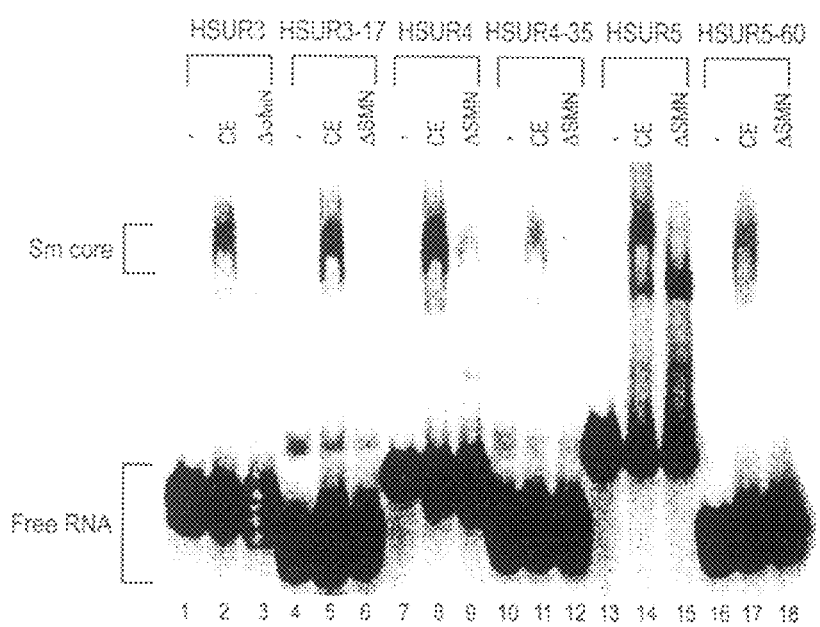

The Minimal SMN Complex-Binding Domains are Sufficient for SMN-Dependent Sm Core Assembly To investigate if the minimal SMN complex-binding domains are sufficient for Sm core assembly, [$^{32}$P]UTP-labeled HSUR3-17, HSUR4-35 and HSUR560 (FIG. 2A) were incubated in HeLa cytoplasmic extracts and the snRNP assembly reaction products were analyzed by electrophoresis on native polyacrylamide gels. The full-length RNAs (HSUR3, HSUR4, and HSUR5) were also labeled and tested in parallel as a positive control. As demonstrated in FIG. 2B, the minimal regions of all three HSURs assemble Sm cores in vitro (lanes 5, 11 and 17) that migrate at a size similar to that of the full-length RNA counterparts (lanes 2, 8 and 14) and super-shift upon addition of anti-Sm monoclonal antibody (Y12). The shorter minimal domains, the 5'-ends of which are indicated by an open arrow (FIG. 2A), do not efficiently assemble Sm cores. For HSUR5, the band that migrates slightly faster than the Sm core band most likely comprises HSUR5 complexed with the HuR protein which binds to AUUUA (SEQ ID NO:2) repeats at the 5' end of HSURs 1, 2, and 5 (FIG. 2B, lanes 14 and 15).

To examine the role of the SMN complex in the assembly of Sm cores on the minimal HSURs, the SMN complex was immunodepleted from cytoplasmic extracts prior to the assembly reaction. For full-length and minimal RNAs alike, the removal of the SMN complex results in loss of Sm core assembly (FIG. 2B lanes 3, 6, 9, 12, 15 and 18), even though immunodepletion of SMN does not significantly reduce the amount of Sm proteins in the extracts (Golembe, 2005, Mol. Cell. Biol. 25: 602-611; Pellizzoni, 2002, Science 298: 1775-1779). It is of note that the minimal domains of HSUR4 (HSUR4-35) and HSUR5 (HSUR5-60) do not assemble Sm cores as efficiently as the full-length RNAs (FIG. 2B, compare lanes 8 and 11, 14 and 17), but this is consistent with and proportional to the reduction in their efficiency of binding to the SMN complex (FIGS. 1E and 1F). These experiments therefore demonstrate that the minimal SMN complex-binding domains are sufficient for Sm core assembly.

Figure 3A:
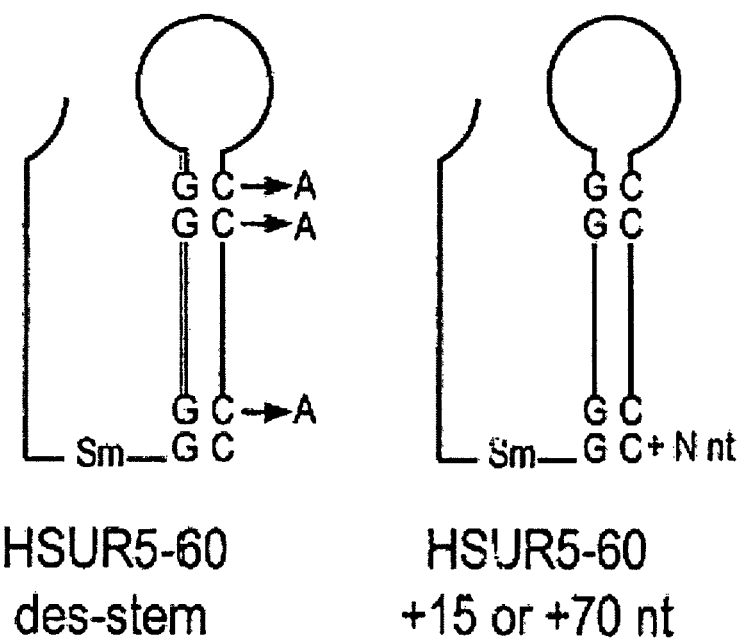
FIGS. 3A through 3E, is a series of images demonstrating that a terminal stem-loop is necessary for SMN complex binding in vitro and Sm core assembly in vivo.
Figure 3B:
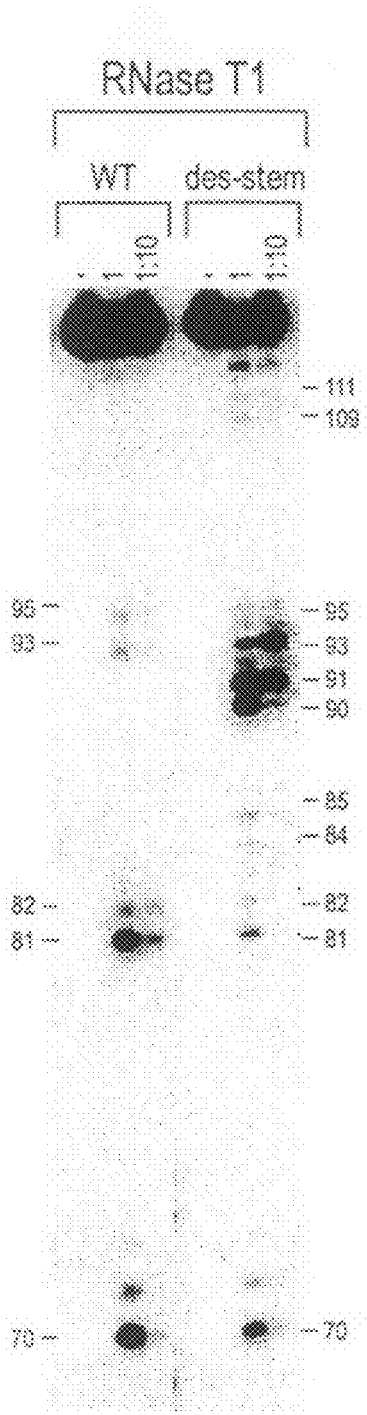

A Terminal 3' Stem-Loop is Required for SMN Complex Binding and Sm Core Assembly The presence of a 3' stem-loop is a common feature of the minimal SMN complex-binding domains of both the HSURs (FIG. 2A) and most of the U snRNAs (Yong, 2004, Mol. Cell. Biol. 24: 2747-2756). Therefore, the importance of the 3' stem-loop for SMN complex binding and Sm core assembly was evaluated. Site-directed mutagenesis was used to destabilize the terminal stem in HSUR5-60 (FIG. 3A, des-stem). Limited RNase T1 digestion, which cleaves 3' of guanosines in single-stranded RNAs, confirmed the linearization of the stem structure (FIG. 3B). In addition, to determine if the stem-loop must be at the 3' end of the RNA, constructs were made that include either 15 or 70 additional nucleotides at the 3'-end of HSUR5-60 (FIG. 3A, +15 nt and +70 nt). The RNAs were then labeled with [$^{32}$P]UTP, mixed with labeled U6 snRNA as a negative control, and tested for binding to purified SMN complex. As demonstrated in FIG. 3C, disruption of the secondary structure of the stem-loop strongly reduces SMN complex binding. In addition, the 3' stem-loop was removed completely (no stem), and this construct also demonstrated a reduction in SMN complex binding. However, the addition of nucleotides to the 3'-end of HSUR5-60 did not impair SMN complex binding (FIG. 3C), presumably because the SMN binding site has itself not been altered (FIG. 2A).

Figure 3C:
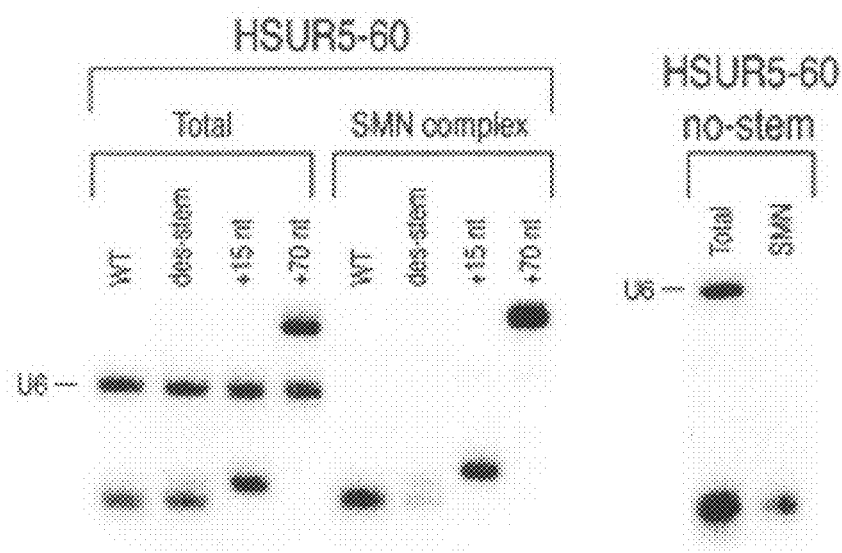
Figures 3D, 3E:
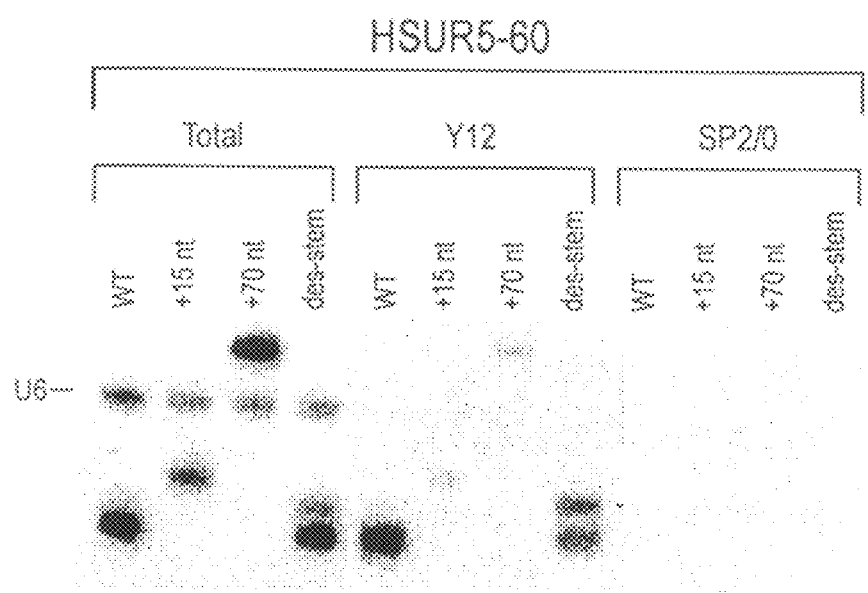

To investigate if the structure and/or the position of the stem-loop affect the assembly of an Sm core in vivo, the des-stem, +15 nt and +70 nt RNAs were $^{32}$P-labeled and microinjected into the cytoplasm Xenopus oocytes (FIG. 3D). After 1.5 hours of incubation, the oocytes were homogenized and immunoprecipitations were carried out with either anti-Sm (Y12) or control non immune (SP2/0) antibodies. RNAs were purified and analyzed by electrophoresis on polyacrylamide gels. Immunoprecipitation of assembled Sm cores with Y12 antibody (anti-SMN antibody) revealed that the des-stem RNA, is less efficient in Sm core assembly (FIG. 3E), consistent with its decreased binding efficiently to the SMN complex in vitro (FIG. 3C). However, the +15 nt and +70 nt HSUR5-60 mutants were significantly deficient in Sm core assembly (FIG. 3E), despite their efficient binding to the SMN complex (FIG. 3C).

Figure 4A:
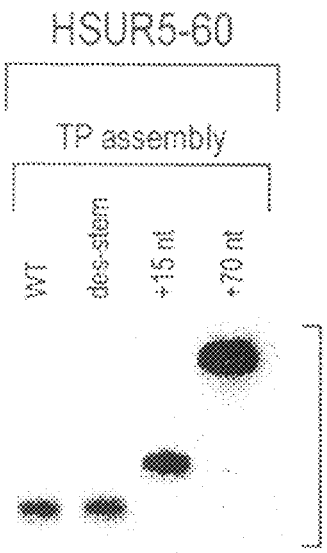
FIGS. 4A through 4E, is a series of images depicting that a terminal stem-loop is required for SMN-dependent Sm core assembly.
Figure 4B:
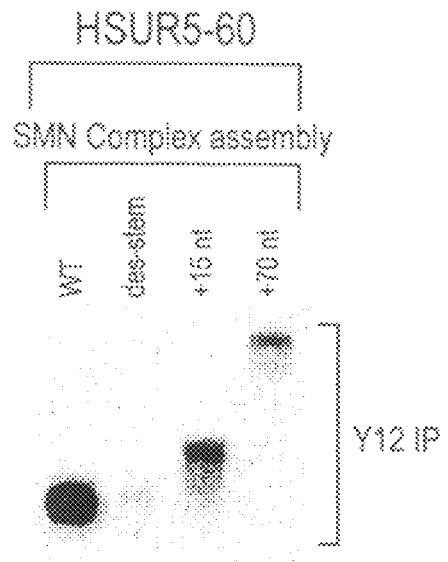
Figure 4C:
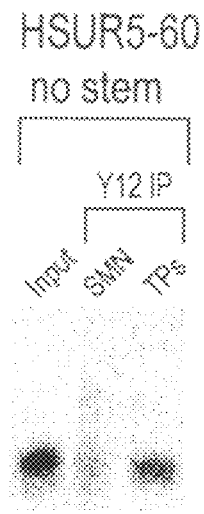
Figure 4D:
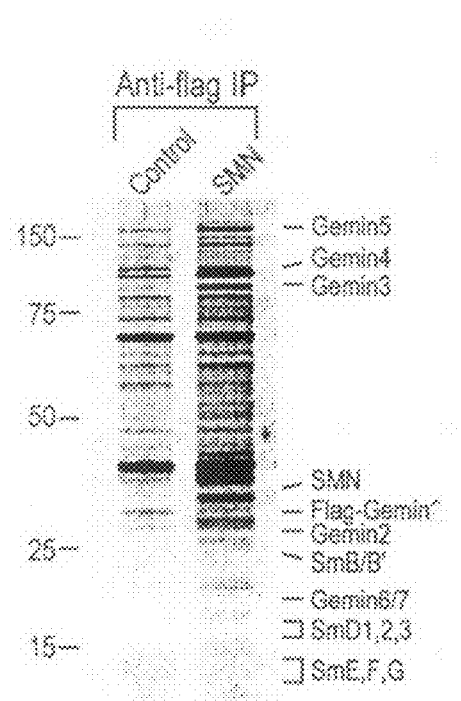
Figure 4E:
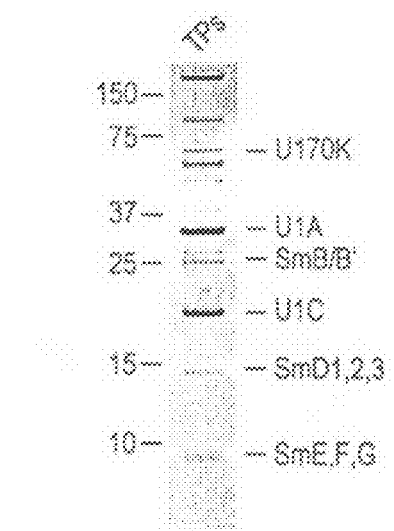

The assembly of the Sm cores on these RNAs in vitro with purified SMN complex or purified snRNP total proteins (TPs) was investigated, as depicted in FIGS. 4D and 4E. Briefly, Flag-purified proteins were eluted with Flag peptides, resolved by electrophoresis on gradient polyacrylamide gels and analyzed by silver stain. Under these conditions, all seven Sm proteins co-purify with the SMN complex. TPs can readily assemble Sm cores on Sm site-containing oligonucleotides alone (Raker, 1999, Mol. Cell. Biol. 19: 6554-6565), and the data disclosed herein demonstrate that Sm cores efficiently assemble on both the des-stem, +15 nt and +70 nt RNAs (FIG. 4A). To assess SMN-mediated Sm core assembly on the same RNAs, SMN complexes were purified under low-salt conditions so that endogenous Sm proteins remained associated (FIG. 4D). SMN-Sm protein complexes are necessary and sufficient for Sm core assembly (Golembe, 2005, Mol. Cell. Biol. 25: 602-611; Pellizzoni, 2002, Science 298: 1775-1779). In contrast to TPs, assembly of Sm cores was drastically reduced on the des-stem, +15 nt and +70 nt RNAs when compared to the wildtype (FIGS. 4B and 4C). Thus, in contrast with TPs, the SMN complex requires a stem-loop 3' of an Sm site for binding, and the SMN complex will only assemble an Sm core efficiently if the stem-loop is located at the 3'-end of the RNA.

Figure 5A:
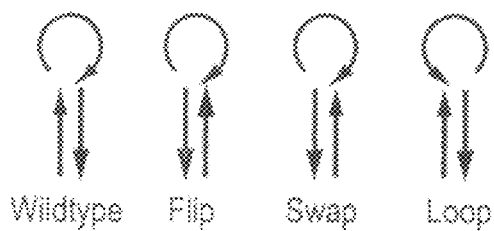
FIGS. 5A through 5D, is a series of images depicting that the sequence of the 3' stem-loop is not critical for SMN complex binding in vitro or Sm core assembly in vivo.
Figure 5B:
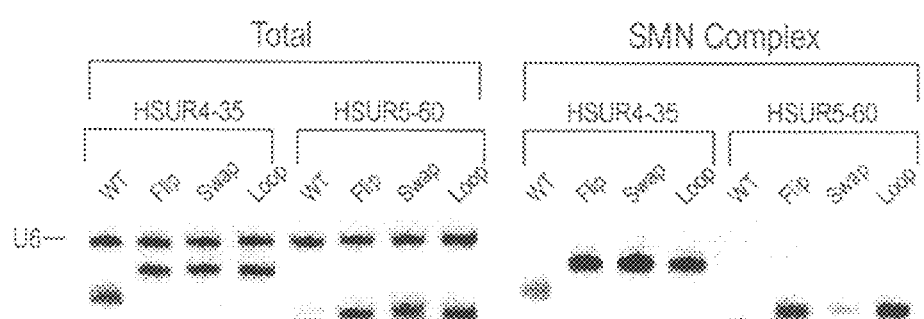

The Sequence of the 3' Stem-Loop is not Critical for SMN Complex Binding and Sm core Assembly To determine if the specific sequence of the stem or the loop is important for SMN complex binding and SMN-medicated Sm core assembly, several mutants were constructed. Specifically, mutants of HSUR4-35 and HSUR5-60 with alterations in the sequences, but not the lengths, of the stem-loop were made. To maintain the base-pairing properties of the stem and the size of the loop, only the directionality of the sequences were changed, so that the stem is either flipped upside-down (flip), the 5' face of the stem is swapped with the 3' face of the stem (swap), or the sequence of the loop is reversed (loop), as illustrated in FIG. 5A. These RNAs were then transcribed in vitro with [$^{32}$P]UTP, mixed with labeled U6 snRNA as a negative control, and incubated with purified SMN complexes or with the corresponding HeLa immunopurified control fractions. Most of the sequence alterations in the stem or the loop of HSUR4-35 and HSUR5-60 had little effect on the binding to the SMN complex (FIG. 5B). Only one construct, HSUR5-60 swap, demonstrated some reduction in SMN complex binding (FIG. 5B). None of the RNAs displayed background binding to the negative control.

Figure 5C:
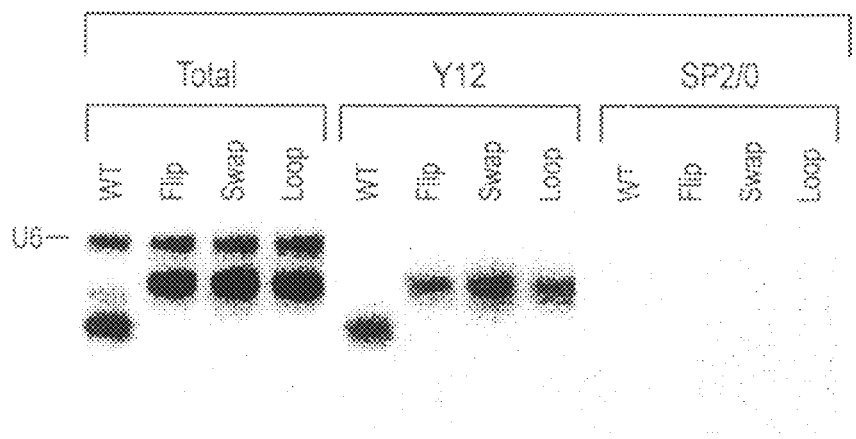
Figure 5D:
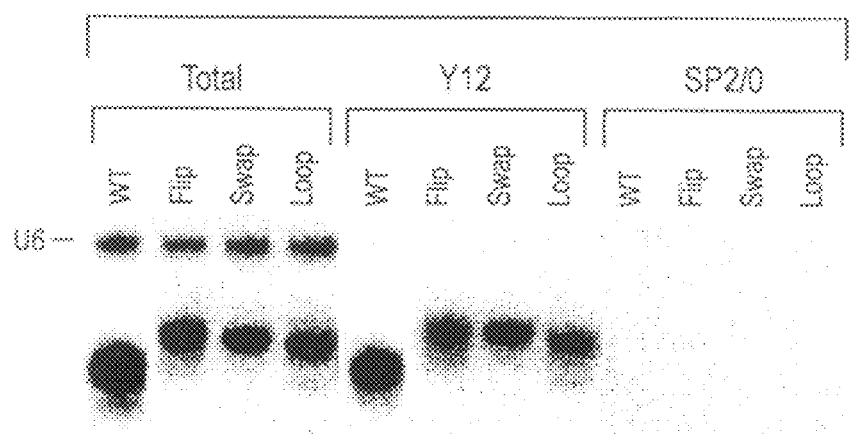

To determine the effects of stem-loop mutations on Sm core assembly, the $^{32}$P-labeled RNAs were microinjected into the cytoplasm of Xenopus oocytes, as described above and depicted in FIG. 3D. Immunoprecipitation with Y12 antibody from total extract revealed that all of the stem-loop mutants of both HSUR4-35 and HSUR5-60 efficiently assemble Sm cores in vivo (FIGS. 5C and D, respectively). As a majority of the sequence changes do not affect SMN complex binding or Sm core assembly, it seems unlikely that the SMN complex recognizes a specific sequence in either the stem or the loop of these RNAs. Rather, the stem-loop appears to be an important structural element required for SMN complex binding.

Figure 6A:
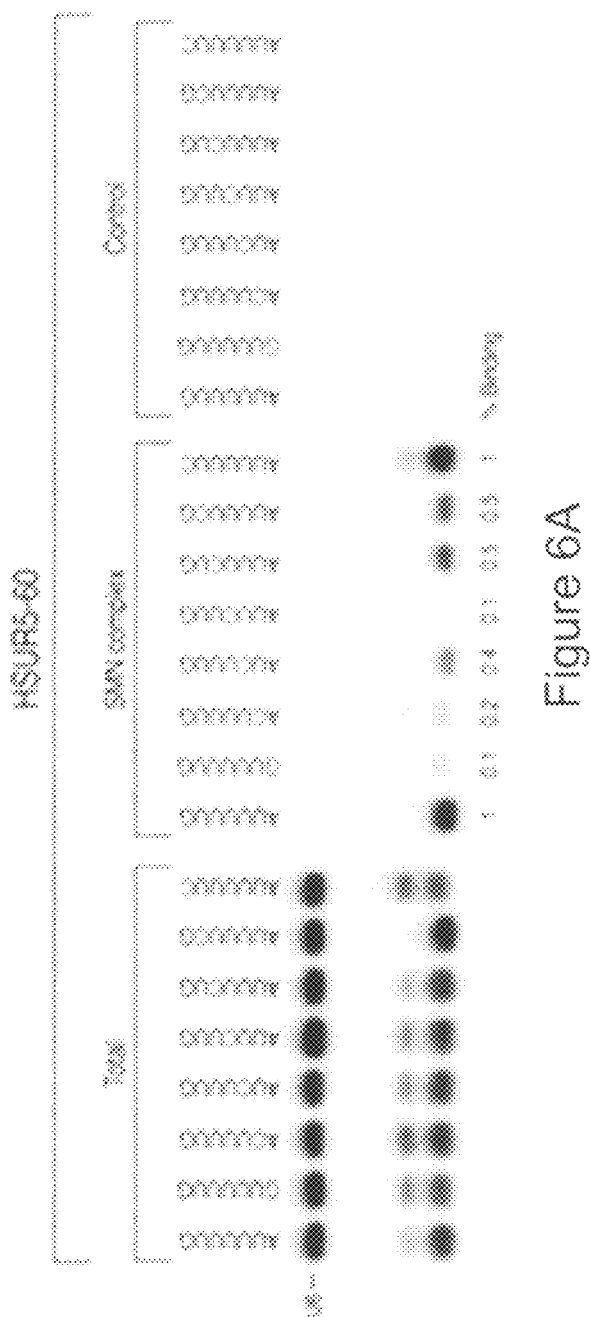
FIGS. 6A through 6C, is a series of images depicting that the first and third uridines of the Sm site are essential for SMN complex binding and Sm core assembly in vitro.

Specific Nucleotides of the Sm Site are Essential for SMN Complex Binding and Sm Core Assembly In addition to the 3' stem-loop, the Sm site is a conserved feature among the minimal SMN complex-binding domains (FIG. 2A) (Yong, 2004, Mol. Cell. Biol. 24: 2747-2756). To determine if the conserved sequence of the Sm site is important for SMN complex binding, mutations were produced in HSURs. Specifically, mutations were generated in the Sm site of HSURS-60 (AUUUUUG; SEQ ID NO: 1) that changed each uridine to a cytosine one at a time, in addition to the adenosine and guanosine, which were changed to a cytosine and adenosine, respectively. The HSUR5-60 mutants were then labeled with [$^{32}$P]UTP, mixed with U6 as a negative control, and bound to purified SMN complexes or nonspecific control proteins. As depicted in FIG. 6, substitution of the first or third uridines of the Sm site severely disrupts SMN complex binding by 80% and 90%, respectively (FIG. 6A), whereas a change in either the second, fourth or fifth uridines decreased SMN complex binding by about 38% to 55% (FIG. 6A). Notably, substitution of the Sm site adenosine also reduces SMN complex binding, whereas a change made to the guanosine had no detectable effect (FIG. 6A). None of the Sm site mutants bound to the negative control.

Figure 6B:
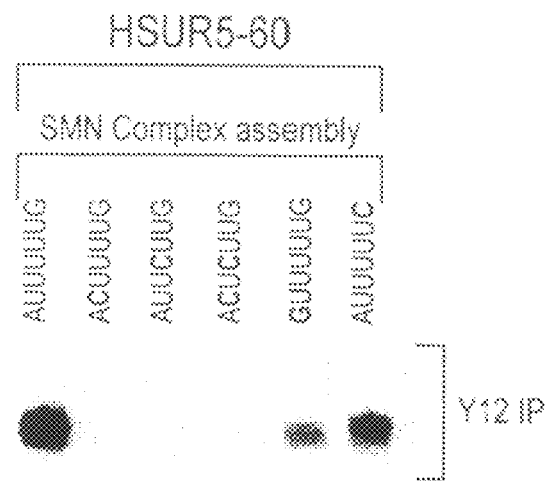
Figure 6C:
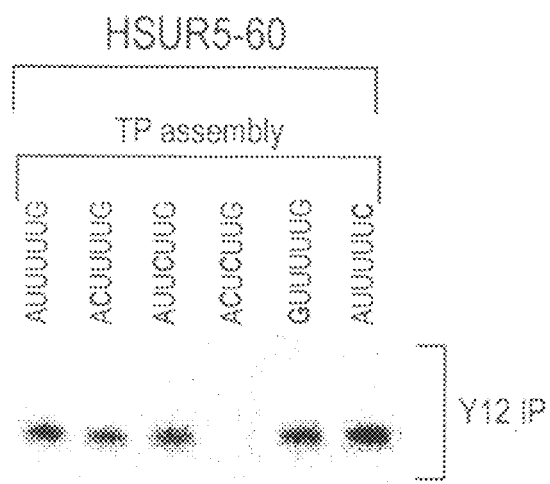

To differentiate between Sm site mutations that interfere with Sm protein binding versus mutations that affect SMN-dependent Sm core assembly, Sm site mutants were incubated with either TPs or low-salt-purified SMN complex. Interestingly, TPs readily assemble an Sm core when any one of the Sm site positions are changed (FIG. 6C), but do not assemble on a mutant that contains a double substitution in both the first and third uridines of the Sm site (FIG. 6C). In contrast, a change to the first and/or third uridines of the Sm site leads to a dramatic reduction in SMN-mediated Sm core assembly (FIG. 6B). The levels of SMN-mediated Sm core assembly are less significantly reduced when the adenosine, second uridine, or fourth uridine positions are changed (FIG. 6B). For all of the Sm site mutants, Sm core assembly is directly proportional to the efficiency of SMN complex binding. While the overall sequence of the Sm site appears to be important, these data demonstrate that the first and third uridines of the Sm site are critical for SMN complex binding.

Figure 7A:
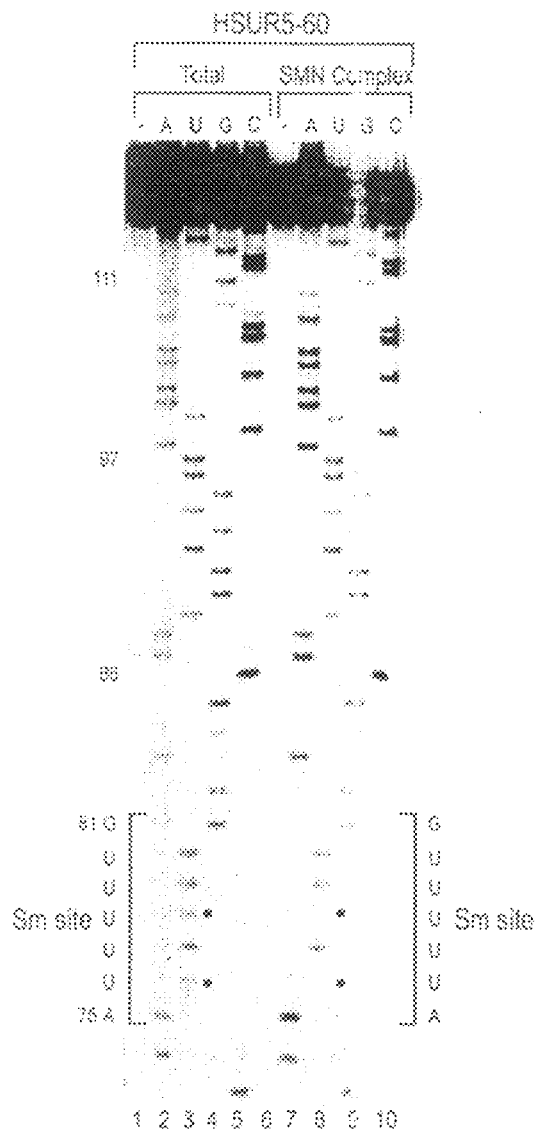
FIGS. 7A through 7D, is a series of images depicting that the SMN complex contacts the phosphate backbone of the first and third uridines of the Sm site.
Figure 7B:
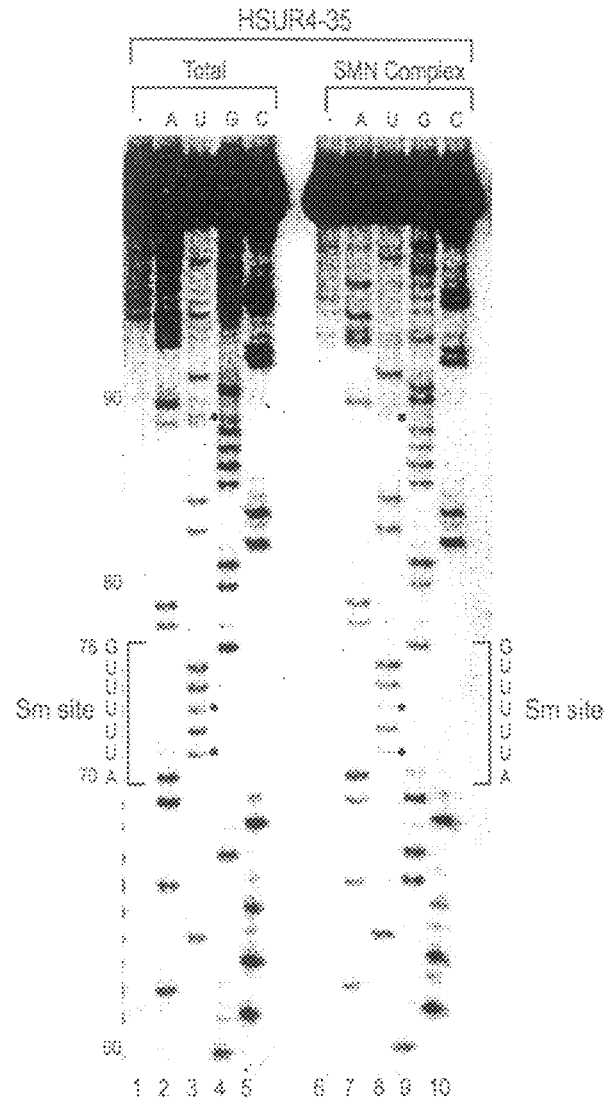
Figure 7C:
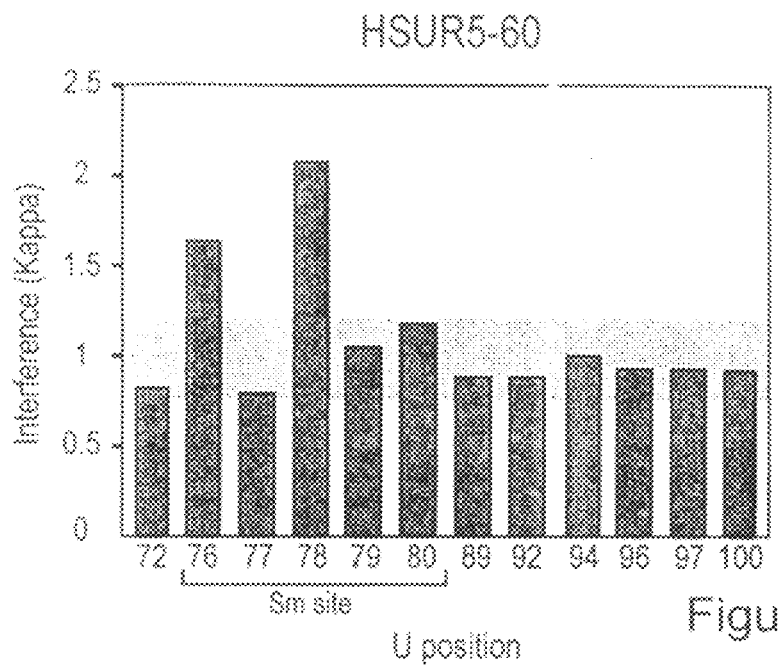
Figure 7D:
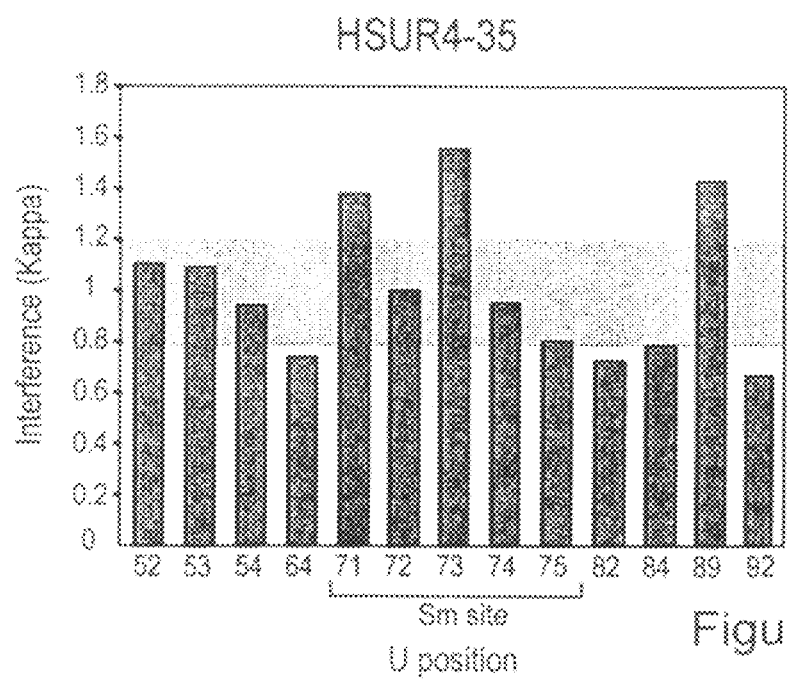

The SMN Complex Contacts the snRNA Backbone at the First and Third Uridines of the Sm Site The sequence of the Sm site is important for SMN complex binding and Sm core assembly. Therefore, the presence of a direct interaction between the SMN complex and this region of the snRNA was investigated. Phosphorothioate interference mapping, which randomly incorporates α-phosphorothioate-tagged nucleotide analogs into the phosphate backbone of an RNA molecule, was used to identify potential interactions of the SMN complex with the RNA backbone. After incorporation, the phosphorothioate linkages are cleaved upon addition of iodine, producing a ladder on a sequencing gel (Ryder, 2000, Methods Enzymol. 317: 92-109). At a position where the substitution interferes with protein binding, a band of lower intensity will be present on the gel that is quantitatively represented as an increased Kappa (κ) value. Likewise, a reduced κ indicates a position of enhancement (Ryder, 2000, Methods Enzymol. 317: 92-109). To identify positions in the HSURs where phosphorothioate substitution affects SMN complex binding, HSUR5-60 and HSUR4-35 were transcribed in the presence of the adenosine (A), uridine (U), guanosine (G) or cytidine (C) α-thiotriphosphates, labeled at the 5'-end with γ-[$^{32}$P]ATP and incubated with high-salt-washed immunopurifed SMN complexes or nonspecifically immunopurified proteins as a control. The purified SMN complex appeared to be free of Sm proteins, as their association is undetectable by both silver stain and Western blot (FIGS. 1A and 8D) (Pellizzoni, 2002, J. Biol. Chem. 277: 7540-7545; Pellizzoni, 2002, Science 298:1775-1779; Yong, 2004, Mol. Cell. Biol. 24: 2747-2756; Yong, 2002, EMBO J. 21: 1188-1196). Bound RNAs were then purified, cleaved with iodine and analyzed by denaturing polyacrylamide gel electrophoresis. FIGS. 7A and 7B depict the sequencing ladders for HSUR5-60 and for HSUR4-35, respectively. It is important to note that only the regions contained within nucleotides 70-114 for HSUR5-60 and 52-92 for HSUR4-35 were analyzed. As a control for phosphorothioate incorporation and cleavage efficiency, an equivalent amount of the total RNAs were treated with iodine and loaded in parallel (FIGS. 7A and 7B). In addition, total and SMN complex-bound RNAs not treated with iodine were analyzed for nonspecific cleavage, which was undetectable. For both HSUR5-60 and HSUR4-35, strong interferences occur at the first and third uridine positions (U at position 76 and U at position 78 in FIG. 7A and U at position 71 and U at position 73 FIG. 7B) of the Sm site, in addition to U at position 89 in the loop of HSUR4-35 (FIG. 7B). The graphs depicted in FIGS. 7C and 7D display the numerical Kappa (κ) values for the uridine positions of the two RNAs, which are increased for the first and third Sm site uridines. Even though the Sm site adenosine also appears to be important for SMN complex binding (FIG. 6C), no specific interference was observed at this position, or at any other A, C or G position within the regions analyzed (FIGS. 7A and B).

Because the HSURs share a common binding site on the SMN complex with U4 snRNA (Golembe, 2005, Mol. Cell. Biol. 25: 602-6114), a similar analysis of the minimal SMN complex-binding domain of U4 snRNA (Yong, 2004, Mol. Cell. Biol. 24: 2747-2756) was performed and also revealed an increase in the κ values for the first and third Sm site uridines. These results clearly indicate that SMN complex recognition of snRNAs does involve direct contact of the phosphate backbone of specific Sm site uridines.

Sm Proteins Alone do not Contact the Phosphate Backbone of Sm Site Uridines

Figure 8A:
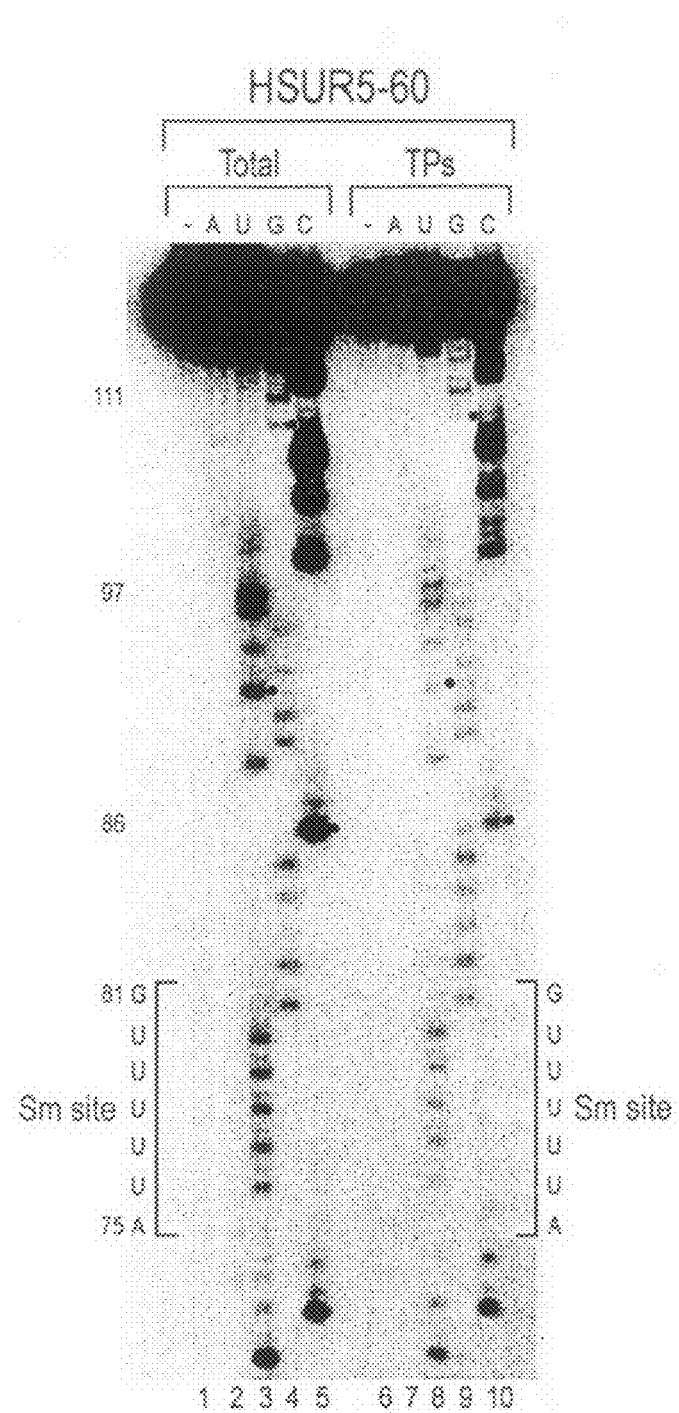
FIGS. 8A through 8D, is a series of images depicting that Sm proteins do not cause phosphorothioate interference at Sm site uridines.
Figure 8B:
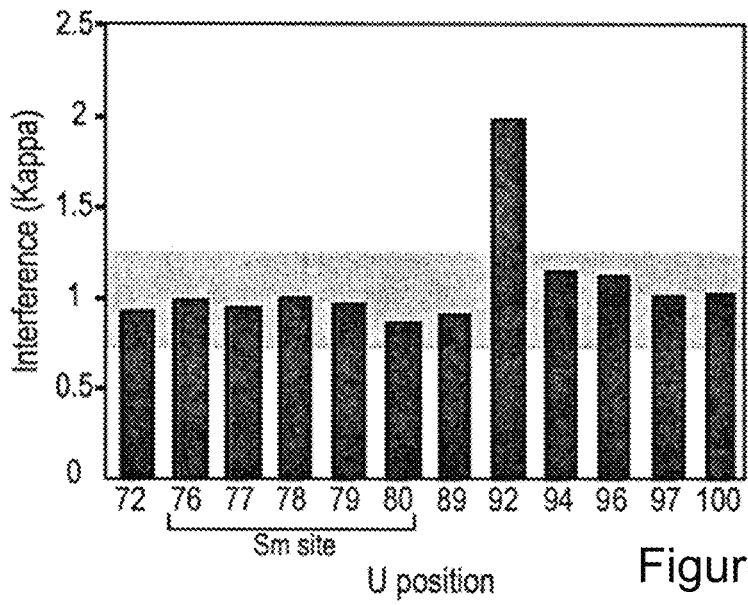
Figure 8C:
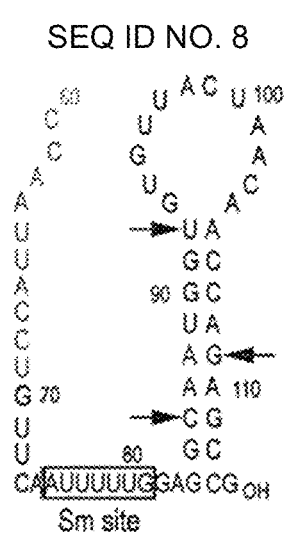
Figure 8D:
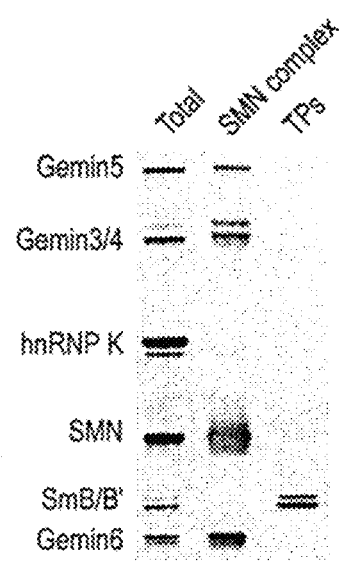

To rule out interference that might be caused by Sm proteins, rather than SMN complex, purified snRNP total proteins (TPs) that contain all seven Sm proteins in addition to U1 snRNP specific proteins (FIG. 4E) were incubated with phosphorothioate-tagged HSUR5-60. RNAs that acquired an Sm core were immunoprecipitated with Y12, cleaved with iodine and analyzed by denaturing polyacrylamide gel electrophoresis. FIG. 8A depicts the resulting sequencing ladder for the region of HSUR5-60 that includes nucleotide 70 thru the 3'-end. Interestingly, the calculated interference (κ) values reveal that the TPs do not contact the phosphate backbone at any position within the Sm site (FIG. 8B). Rather, interferences were observed only at positions outside of the Sm site, including U at position 92, C at position 86 and G at position 109 within the region analyzed (FIG. 8C). Importantly, the pattern of interference caused by TPs is completely different from that of the SMN complex (compared in FIGS. 7 and 8), and the TPs used in this experiment do not contain any obvious traces of SMN complex components (FIG. 8D). This experiment demonstrates that direct contact of the Sm site is due to SMN complex, rather than Sm protein, interactions with the snRNA.

Figure 9:
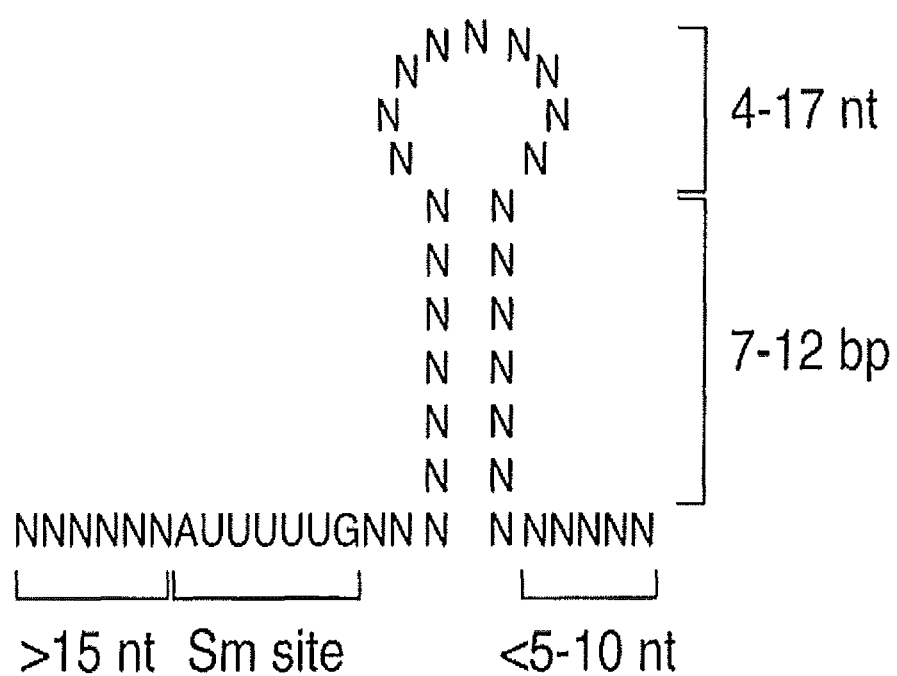
FIG. 9, is a schematic depicting the essential sequence and structural features of an isolated snRNA (SEQ ID NO. 9). The Sm site, stem-loop and portion comprising a >15 nucleotide (nt) nucleic acid cargo located on the 5' end of the molecule are indicated.

Other data indicated that the process of snRNP assembly, particularly the formation of the highly stable Sm core, is not a self-assembly process as had been widely believed, but rather is an active process mediated by the SMN complex (Buhler, 1999, Hum. Mol. Genet. 8: 2351-2357; Fischer, 1997, Cell 90: 1023-1029; Liu and Dreyfuss, 1996, EMBO J. 15: 3555-3565; Liu, 1997, Cell 90: 1013-1021; Meister, 2001, Nat. Cell. Biol. 3: 945-949; Meister, 2002, Trends Cell Biol. 12: 472-478; Meister and Fischer, 2002, EMBO J. 21: 5853-5863; Pellizzoni, 1998, Cell 95: 615-624; Pellizzoni, 2002, Science 298: 1775-1779; Yong, 2004, Mol. Cell. Biol. 24: 2747-2756; Yong, 2002, EMBO J. 21: 1188-1196; Yong, 2004, Trends Cell Biol. 14: 226-232). Cells employ the SMN complex for snRNP assembly to prevent the potentially promiscuous Sm proteins from forming Sm cores indiscriminately and ensure that Sm cores would only assemble on the correct RNAs (Pellizzoni, 2002, Science 298: 1775-1779; Yong, 2004, Mol. Cell. Biol. 24: 2747-2756). Subsequent experiments (Yong, 2004, Mol. Cell. Biol. 24: 2747-2756; Yong, 2002, EMBO J. 21: 1188-1196) delineated the general domains in the major snRNAs, U1, U2, U4 and U5, that must contain the specific binding sites for the SMN complex. However, because there is no extensive sequence similarity among the SMN complex-binding domains of these snRNAs, the means by which the SMN complex distinguishes them from other cellular RNAs remained unclear. The HSURs, the snRNAs encoded by HVS, provide an attractive system to address this question because they use the SMN complex to assemble Sm cores, bind the SMN complex with high affinity, have considerable sequence conservation among them, and bear a striking resemblance to the overall structure of several of the major snRNAs (Golembe, 2005, Mol. Cell. Biol. 25: 602-611; Lee, 1988, Cell 54: 599-607; Lee, 1990, J. Virol. 64: 3905-3915). By systematic mutagenesis of the HSURs and using several experimental approaches, the data disclosed herein demonstrates the critical RNA sequence features that confer binding to the SMN complex and assembly of an Sm core. These data revealed a structural configuration comprising an Sm site (AUUUUUG; SEQ ID NO: 1) and a 3' terminal stem-loop that is critical for Sm core assembly in vitro and in vivo. These structural features, illustrated in FIG. 9, are independent of RNA sequence. This motif constitutes a snRNP code that is recognized by direct binding to the SMN complex and triggers formation of the Sm core on the Sm site.

Viewed in the more general context of how cells distinguish among the different classes of RNAs, the present invention reveals a clear signature in the major snRNAs and demonstrates that the SMN complex performs the task of identifying that signature as well as directing the assembly of these RNAs into the corresponding RNPs. That is, the data disclosed herein demonstrates that it is the SMN complex itself, and not the Sm proteins on their own, that is responsible for deciphering this snRNP code. Further, the present invention demonstrates that binding to the SMN complex, while necessary, is not sufficient for Sm core assembly. The minimal SMN complex-binding domains of the HSURs employed in the present invention are conserved (FIG. 2A), structurally resemble those of the major Sm site-containing U snRNAs, U2, U4 and U5 (Yong, 2004, Mol. Cell. Biol. 24: 2747-2756), and assemble SMN-dependent cores. Further, the HSURs provide a tool to identify the essential structural elements required for SMN complex binding and activity and provide stable, specific and nuclear-targeting compositions for gene inhibition. As disclosed herein, the Sm sequence itself is an important determinant for how the SMN complex binds to an snRNA. Of the known Sm site-containing U RNAs, including the HSURs, only U1 snRNA diverges in its Sm site sequence from PuAU4-6GPu to AAUUUCUGG (SEQ ID NO: 3). Consequently, U1 snRNA binds to the SMN complex through a sequence at its 5'-, rather than 3'-, end and at an independent binding site on the SMN complex (Golembe, 2005, Mol. Cell. Biol. 25: 602-611; Yong, 2004, Mol. Cell. Biol. 24: 2747-2756), while the other U snRNAs and the HSURs share a second binding site. Only two snRNA binding sites have been identified on the SMN complex thus far, however, it is possible that additional or more complicated modes of binding exist. Nevertheless, it is clear that the strong majority of snRNAs fall within a single class of PuAU4-6GPu-type Sm site RNAs that share a common mode of binding to the SMN complex.

The data disclosed herein demonstrates that the SMN complex specifically contacts the RNA backbone of the first and third uridines of the Sm site. Although previous studies have demonstrated that SmG and SmB/B', respectively, cross-link to these same positions in vitro (Urlaub, 2001, EMBO J. 20: 187-196), the SMN complex used for direct binding experiments is free of any detectable Sm proteins (FIGS. 1A and 8D) and is not competent for the assembly of Sm cores in vitro. Further, the present data demonstrates that the assembly activity of purified TPs is more promiscuous than that of purified. SMN complex (FIGS. 4 and 6) and that TPs alone contact only the backbone of the 3' stem-loop, but not Sm site uridines (FIG. 8). This interference data is consistent with the previous report that TPs interact with the backbone of the 3' stem-loop of U1 snRNA, but not at nucleotide positions within the Sm site (McConnell, 2003, RNA 9: 193-2013). Therefore, the present data represents Sm protein, rather than SMN complex-dependent, interactions with snRNAs. In vivo, Sm proteins are not free, but are associated with a number of protein complexes, including the 6S PIC1n-containing complex and the 20S methylosome (Friesen, 2001, Mol. Cell 7: 1111-1117; Friesen, 2002, J. Biol. Chem. 277: 8243-8247; Meister, 2001, Nat. Cell. Biol. 3: 945-949; Pu, 1999, Mol. Cell. Biol. 19: 4113-4120). Because only Sm proteins that are carried by the SMN complex are competent for Sm core assembly (Pellizzoni, 2002, Science 298: 1775-1779; Pu, 1999, Mol. Cell. Biol. 19: 4113-4120), it follows that the SMN complex might contact the very same site upon which Sm proteins assemble. This mechanism of surveillance explains how the SMN complex ensures that Sm cores assemble only on the correct RNA targets (Pellizzoni, 2002, Science 298: 1775-1779), and further elucidates the specificity of the present invention.

The data disclosed herein demonstrate that the SMN complex recognizes the Sm site of an snRNA when it is presented within the context of a 3' stem-loop. Upon destabilization or removal of the stem-loop, SMN complex binding and SMN-mediated Sm core assembly are dramatically reduced. However, in contrast to the critical uridines of the Sm site, the sequence of the stem-loop seems to be relatively unimportant (FIGS. 3 and 4). Considering the stem-loop sequences of the U snRNAs and HSURs do not appear to have extensive sequence conservation both within and between the two groups, this feature adds flexibility to the present invention. Furthermore, five variants of U5 snRNA exist within cells that have various changes throughout their stem-loop sequences that do not affect their assembly into snRNPs (Sontheimer and Steitz. 1992, Mol. Cell. Biol. 12: 734-746).

Another requirement for SMN-mediated Sm core assembly, as demonstrated herein, is the location of the stem-loop at the terminal end of the snRNA. Interestingly, the SMN complex will bind to snRNAs that have extensions at the 3'-end, but will not assemble Sm cores on them (FIGS. 3 and 4). Thus, the nucleic acids of the present invention permit the introduction of additional molecules, such as antisense molecules, RNA-binding protein decoys, siRNA, and the like.

Overall, the present invention demonstrates that to be recognized as an snRNA destined to receive an Sm core, a cellular RNA must present to the SMN complex a PuAU4-6GPu-type Sm site flanked by a 3' terminal stem-loop.

Example 2

Figure 10:
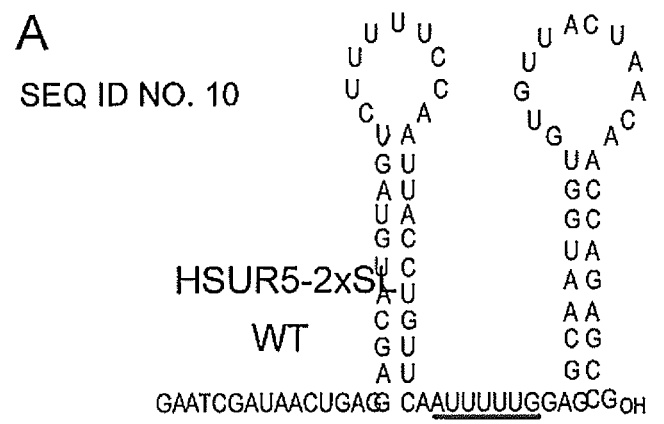
FIG. 10, comprising
Figure 10:
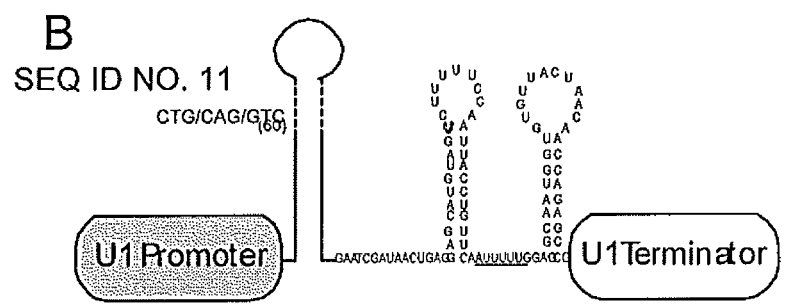

A Recombinant snRNA Comprising Delivers Cargo Nucleotide Sequences to the Nucleus A minimal HSUR sequence (HSUR5-2×SL WT) comprised of 2 stem-loop regions flanking an sm site (FIG. 10A) has been inserted in a mammalian expression vector under the control of the transcriptional cassette of U1 snRNA. At the 5' end of HSUR5-2×SL, in the same promoter setting, has been inserted a cargo sequence of 60 trinucleotide repeats (CTG, CAG, GTC) for a total of approximately 200 nucleotides (FIG. 10B).

HEK293T cells were transfected with the indicated plasmids. RNA was isolated from the cells 60 hrs after transfection and 20 µg of RNA was loaded on a 7M urea-6% polyacrylamide gel. The RNA was then blotted on a Nylon membrane and detected by Northern blotting hybridization with a terminal radiolabeled oligonucleotide probe complementary to HSUR5.

Figure 11:
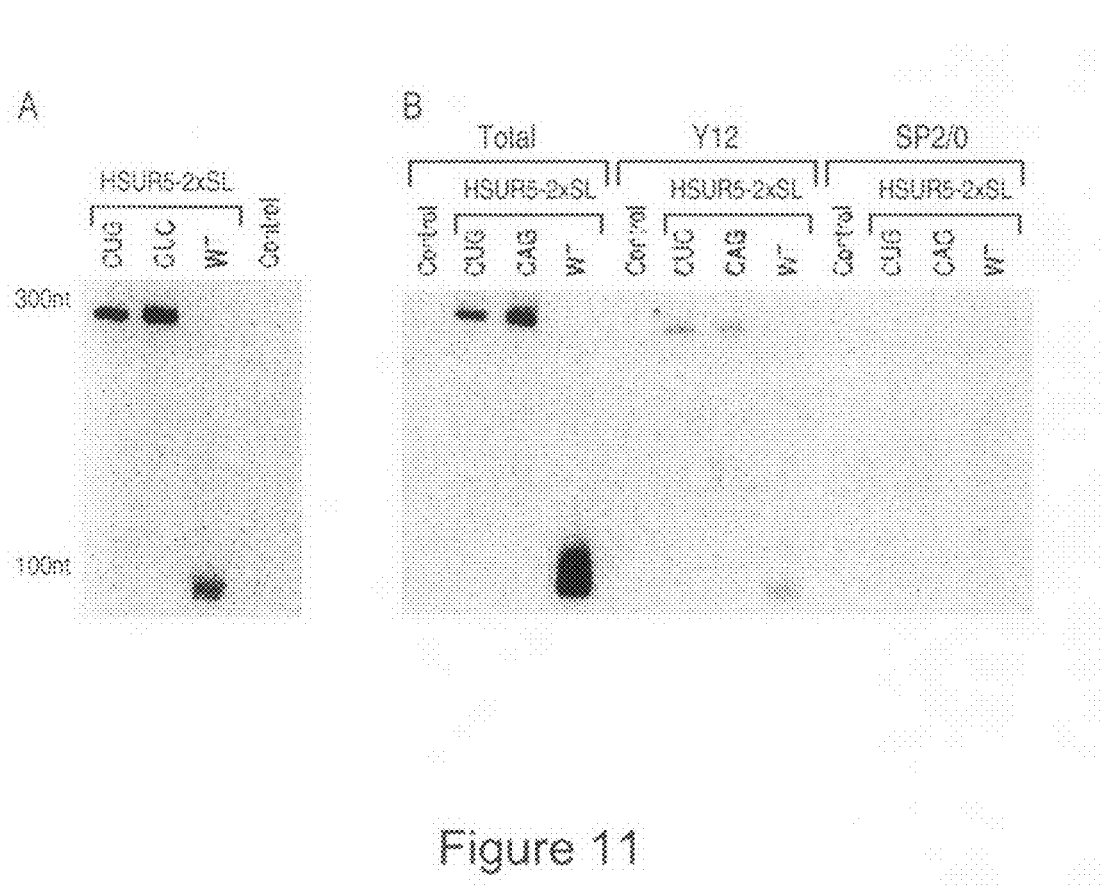
FIG. 11, comprising

Upon transfection of these plasmids in mammalian cells, the U1 promoter drives the transcription of these RNAs (FIG. 11A). The HSUR RNA at the 3' end of these long RNAs will ensure the formation of an sm core on these RNAs hence guaranteeing stability and correct localization (FIG. 11B). HEK293T cells were transfected with the indicated plasmids. At 48 hrs posttransfection, cells were harvested by scraping into ice-cold phosphate-buffered saline, washed twice, and pelleted. Immunoprecipitation experiments were carried out as described in Golembe 2005, Mol. Cell. Biol. 25: 602-611). The isolated RNA was then subjected to Northern Blotting. The long stretch of trinucleotide repeats will fold into stem-loop like secondary structures that are known to bind and sequester RNA binding proteins (e.g. MBNL1) therefore modulating the activity of these RNA binding proteins.

Example 3

Construction of an Artificial, Recombinant snRNA

Artificial snRNAs (Hyb WT, Swap1, Swap2 and Swap 1/2) were synthesized as DNA oligonucleotides (Invitrogen) and cloned into plasmids under the control of the transcriptional cassette of U1 snRNA. Hyb WT is composed of 5' stem-loop of HSUR3 (from nt 7 to nt 24) and 3' stem-loop of HSUR4 (from nt 68 to nt 106).

Swap1ΔSm, Swap1, Swap2, Swap1/2 are as in Hyb WT with the 5' face of the stem (1, 2 or both respectively) swapped with the 3' face of the stem. Swap1ΔSm is the same as Swap1, but with the Sm sequence deleted.

HEK293T were transfected (calcium phosphate method) with 20 µg of the indicated plasmid. At 48 hrs posttransfection, cells were harvested by scraping into ice-cold phosphate-buffered saline, washed twice and pelleted. Immunoprecipitations were carried out as described. The isolated RNA was then subjected to Primer Extension analysis (FIG. 12).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A composition comprising a nucleic acid cargo sequence and an isolated snRNA, wherein said cargo sequence is linked to said snRNA, further wherein said snRNA consists of:
   (a) an Sm site, wherein said Sm site is selected from the group consisting of SEQ ID NO. 1, SEQ ID NO. 2, and SEQ ID NO. 3;
   (b) a stem-loop structure positioned 3' to said Sm site, wherein the number of nucleotides between the Sm site and the 3' stem loop is between 1 and 5 nucleotides, further wherein said stem-loop structure comprises from about 7 to about 12 base pairs in the stem and from about 4 to about 17 nucleotides in the loop; and
   (c) nucleotides located 3' from the stem-loop structure consisting of 5-10 nucleotides.

2. The composition of claim 1, wherein said cargo sequence is an antisense oligonucleotide.

3. The composition of claim 1, wherein said cargo sequence is a small interfering RNA (siRNA).

4. The composition of claim 1, wherein said cargo sequence is a splice-switching oligonucleotide.

5. The composition of claim 1, wherein said cargo sequence is an RNA binding protein decoy.

6. A pharmaceutical composition comprising the isolated snRNA of claim 1.

7. A kit for modulating the expression of a gene in a cell, said kit comprising a composition comprising a nucleic acid cargo sequence and an isolated snRNA, wherein said cargo sequence is linked to said snRNA, further wherein said snRNA consists of:
  (a) an Sm site, wherein said Sm site is selected from the group consisting of SEQ ID NO. 1, SEQ ID NO. 2, and SEQ ID NO. 3;
  (b) a stem-loop structure positioned 3' to said Sm site, wherein the number of nucleotides between the Sm site and the 3' stem loop is between 1 and 5 nucleotides, further wherein said stem-loop structure comprises from about 7 to about 12 base pairs in the stem and from about 4 to about 17 nucleotides in the loop; and
  (c) nucleotides located 3' from the stem-loop structure consisting of 5-10 nucleotides;
wherein, said kit further comprising an applicator and an instructional material for the use thereof.

8. An isolated molecule consisting of a nucleic acid cargo sequence and an isolated snRNA, wherein said snRNA:
  (a) an Sm site, wherein said Sm site is selected from the group consisting of SEQ ID NO. 1, SEQ ID NO. 2, and SEQ ID NO. 3;
  (b) a stem-loop structure positioned 3' to said Sm site, wherein the number of nucleotides between the Sm site and the 3' stem loop is between 1 and 5 nucleotides, further wherein said stem-loop structure comprises from about 7 to about 12 base pairs in the stem and from about 4 to about 17 nucleotides in the loop; and
  (c) nucleotides located 3' from the stem-loop structure consisting of 5-10 nucleotides.

* * * * *